(12) United States Patent
Yokosawa et al.

(10) Patent No.: US 11,701,025 B2
(45) Date of Patent: Jul. 18, 2023

(54) MAGNETIC RESONANCE IMAGING APPARATUS WITH AUTO-POSITIONING FUNCTION, METHOD FOR CONTROLLING MAGNETIC RESONANCE IMAGING APPARATUS, AND PROGRAM FOR AUTO-SETTING OF IMAGING PLANE

(71) Applicant: Hitachi, Ltd., Tokyo (JP)

(72) Inventors: Suguru Yokosawa, Tokyo (JP); Hisaaki Ochi, Tokyo (JP); Yoshimi Noguchi, Tokyo (JP); Kenta Sakuragi, Tokyo (JP); Hisako Nagao, Tokyo (JP); Kuniaki Harada, Tokyo (JP)

(73) Assignee: FUJIFILM Healthcare Corporation, Kashiwa (JP)

( * ) Notice: Subject to any disclaimer, the term of this patent is extended or adjusted under 35 U.S.C. 154(b) by 461 days.

(21) Appl. No.: 16/385,104

(22) Filed: Apr. 16, 2019

(65) Prior Publication Data
US 2020/0008702 A1    Jan. 9, 2020

(30) Foreign Application Priority Data

Jul. 9, 2018 (JP) ................................. 2018-129758

(51) Int. Cl.
*A61B 5/055* (2006.01)
*G01R 33/56* (2006.01)
(Continued)

(52) U.S. Cl.
CPC .............. *A61B 5/055* (2013.01); *A61B 5/742* (2013.01); *A61B 5/7485* (2013.01);
(Continued)

(58) Field of Classification Search
CPC ....... A61B 5/055; A61B 5/7485; A61B 5/742; A61B 2576/00; G01R 33/5608;
(Continued)

(56) References Cited

U.S. PATENT DOCUMENTS

| 2009/0252391 A1* | 10/2009 | Matsuda ............... G16H 30/40 |
| | | 382/131 |
| 2012/0126812 A1* | 5/2012 | Nitta .................. G01R 33/4833 |
| | | 324/309 |
| 2014/0191756 A1* | 7/2014 | Yokosawa ............ A61B 5/0037 |
| | | 324/318 |

(Continued)

FOREIGN PATENT DOCUMENTS

| JP | WO2010-150783 A | 12/2012 |
| JP | 2014-121598 A | 7/2014 |

(Continued)

OTHER PUBLICATIONS

Cai et al. 2015 IEEE Transactions on Medical Imaging 34:1676-1693 (Year: 2015).*

(Continued)

*Primary Examiner* — Keith M Raymond
*Assistant Examiner* — Patrick M Mehl
(74) *Attorney, Agent, or Firm* — Foley & Lardner LLP

(57) ABSTRACT

An imaging unit of an MRI apparatus performs imaging of a positioning image of a subject including a spine; a first imaging that images a cross section including the spine and extending along a longitudinal direction of the spine; and a second imaging that images a cross section in a direction of traversing the spine. An automatic cross-section position setting unit detects a specific tissue of the spine using a scout image or an image including the spine acquired in the first imaging step, performs a matching process between the detected specific tissue of the spine and a spine model, and calculates an imaging cross-section position of the second imaging based upon a specific tissue position of the spine specified by matching, thereby performing automatic setting.

16 Claims, 20 Drawing Sheets

(51) Int. Cl.
  *G01R 33/483* (2006.01)
  *G06T 7/73* (2017.01)
  *A61B 5/00* (2006.01)

(52) U.S. Cl.
  CPC ..... *G01R 33/4833* (2013.01); *G01R 33/5608* (2013.01); *G06T 7/74* (2017.01); *A61B 2576/00* (2013.01); *G06T 2207/10088* (2013.01); *G06T 2207/20081* (2013.01); *G06T 2207/30012* (2013.01)

(58) Field of Classification Search
  CPC .... G01R 33/4833; G01R 33/543; G06T 7/74; G06T 2207/10088; G06T 2207/20081; G06T 2207/30012
  See application file for complete search history.

(56) References Cited

U.S. PATENT DOCUMENTS

| | | | |
|---|---|---|---|
| 2015/0260814 A1 | 9/2015 | Sakurai | |
| 2016/0063720 A1* | 3/2016 | Han | G06F 16/583 382/131 |
| 2016/0071270 A1* | 3/2016 | Shinoda | G06T 11/003 382/131 |
| 2017/0319167 A1* | 11/2017 | Goto | A61B 6/5205 |

FOREIGN PATENT DOCUMENTS

| | | |
|---|---|---|
| JP | WO2013-027540 A | 3/2015 |
| JP | 2015-131023 A | 7/2015 |
| JP | 2017-189233 A | 10/2017 |
| WO | WO-2009/019630 | 2/2009 |
| WO | WO-2010/150783 A1 | 12/2010 |
| WO | WO-2013/027540 A1 | 2/2013 |

OTHER PUBLICATIONS

Kirschner et al. 2011 Proc. SPIE ISOE Prog. Biomed. Optics Imaging 7962:796211 9 pages (Year: 2011).*
Weiss et al. 2006 Radiology 239:255-262 (Year: 2006).*
Pekar et al. 2007 MICCAI 2007, Part I, LNCS 4791, pp. 601-608 (Year: 2007).*
Liao et al. 2017 Journal of Healthcare Engineering article 8691505 12 pages (Year: 2017).*
Office Action issued in corresponding JP Application No. 2018-129758 dated Jul. 19, 2022 (7 pages).
Weiss et al. (Apr. 2006). Automated spine survey iterative scan technique. Radiology, 239(1) pp. 255-262.
Office Action issued in corresponding Japanese Application No. 2018-129758 dated Jan. 11, 2022 with English translation.

* cited by examiner

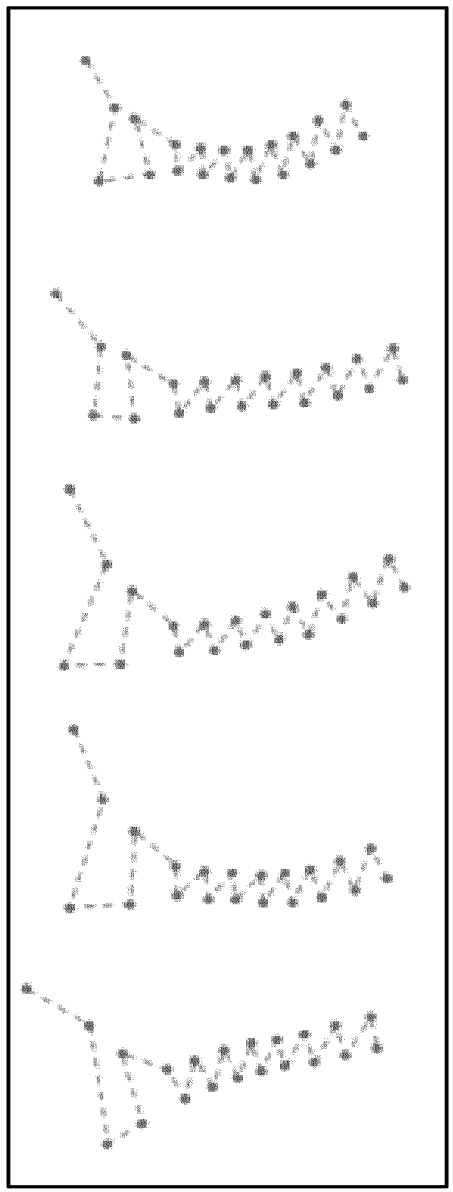
Fig. 9B Deformed model
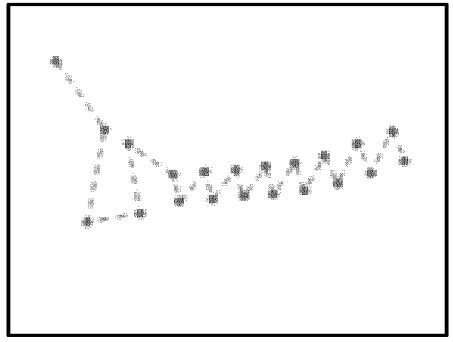
Fig. 9A Mean model

Fig. 15B

| 1 | -2 | 1 |
|---|----|---|
| 2 | -4 | 2 |
| 1 | -2 | 1 |

Fig. 15A

| 2 | 4 | 5 | 4 | 2 |
|---|---|----|---|---|
| 4 | 9 | 12 | 9 | 4 |
| 5 | 12 | 15 | 12 | 5 |
| 4 | 9 | 12 | 9 | 4 |
| 2 | 4 | 5 | 4 | 2 |

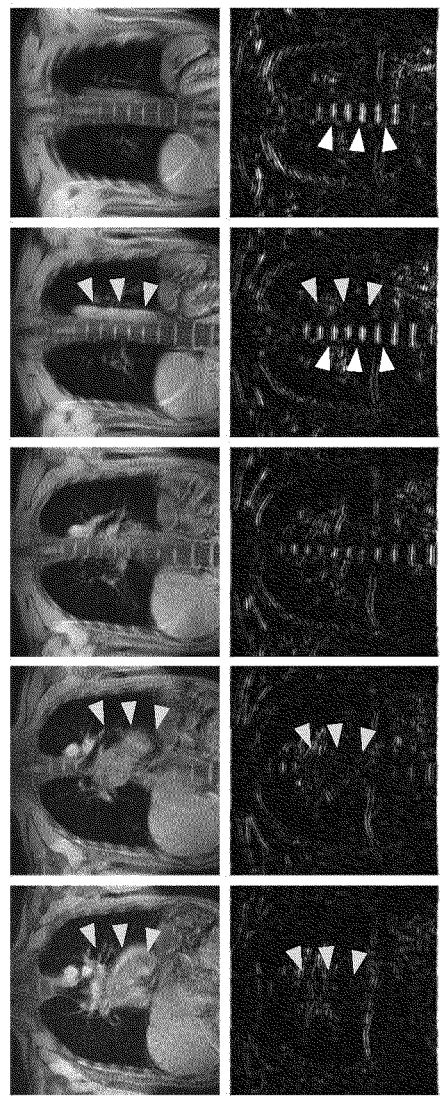

MAGNETIC RESONANCE IMAGING APPARATUS WITH AUTO-POSITIONING FUNCTION, METHOD FOR CONTROLLING MAGNETIC RESONANCE IMAGING APPARATUS, AND PROGRAM FOR AUTO-SETTING OF IMAGING PLANE

BACKGROUND OF THE INVENTION

1. Field of the Invention

The present invention relates to an MRI apparatus having a function of automatically determining an imaging plane of a subject in an examination using a magnetic resonance imaging apparatus (hereinafter referred to as an MRI apparatus).

2. Description of the Related Art

Generally, in an MR examination, after imaging a scout image for confirming a position of an examination part, an operator sets an imaging plane of the examination part on a screen on which the scout image is displayed. As the scout image, for example, a two-dimensional image is acquired which has three-axis planes of a sagittal (SAG) plane, a coronal (COR) plane, and an axial (AX) plane. When the examination part is a spine or an intervertebral disk, since the spine is curved in a front and rear direction (Anterior-Posterior), and a body axial direction (head-to-foot direction: HF direction) of the subject and an up and down direction of the image do not necessarily coincide with each other even in a left and right direction, it is required to specify a desired imaging plane using a plurality of tree-axis planes, respectively, and thus it takes time to determine the position of the imaging plane. Particularly, in the MR examination, even for a single examination part, since a plurality of kinds of imaging, for example, imaging of a T2 weighted image and imaging of a T1 weighted image are performed on a plurality of axial cross sections according to a predetermined protocol, determining the position of the imaging plane for each imaging leads to the extension of imaging time, which is not desirable.

With respect to the above-described problem, there is proposed a technology (hereinafter referred to as an automatic positioning technology) that automatically sets the position of an imaging plane using an anatomical feature of an examination part (for example, JP-A-2014-121598). In the automatic positioning technology, a cross-section position including the examination part is set from the scout image using the anatomical feature of the examination part which can be automatically discriminated from the image. Specifically, the anatomical feature (a feature of an intervertebral disk in the case of a spine) serving as a mark of positioning is automatically extracted by an image recognition technology on the scout image, and the cross section including the extracted anatomical feature is specified. Methods such an object extraction method, a template matching method, and the like are used in an image recognition method.

The object extraction method used in the above-described automatic positioning technology has an advantage in that a calculation speed is fast, however, since accuracy thereof is low, it is essentially required to perform a process for detection omission and excessive detection. On the other hand, in the case of a spine, the template matching method can prevent the detection omission by performing matching on the whole shapes of the spine, however, the template matching method is easy to fall into a local solution in the process of calculation of a matching process for an optimum position, and thus accuracy is unstable.

Particularly, when the examination part is the spine, since there are many cases in which a spine structure is changed by a lesion, it is difficult to accurately extract the intervertebral disk, and the like to set an imaging position. Further, since an individual difference in a spine shape is large, a template having a fixed shape cannot be used. When a reference template is deformed for each examination target and the deformed template is used therefor, since the number of adjustment parameters for the deformation thereof increases, the calculation time is prolonged, and further, the method using the reference template is easy to fall into the local solution.

SUMMARY OF THE INVENTION

Here, an object of the present invention is to provide a technology capable of setting an imaging position (an imaging cross-section position) at a high speed and with high accuracy in an MR examination. Further, an object of the present invention is to provide a technology capable of automatically setting a cross section traversing a spine with high accuracy, particularly in imaging whose target is the spine.

In order to achieve the above-described object, the present invention detects a specific tissue in an image for positioning and executes a matching process on the detected tissue.

That is, an MRI apparatus according to the present invention includes: an imaging unit that selects a desired imaging plane of a subject to acquire a nuclear magnetic resonance signal generated from the imaging plane; a signal processing unit that processes the nuclear magnetic resonance signal acquired from the imaging unit; a control unit that controls the imaging unit and the signal processing unit; and an imaging cross-section position setting unit that automatically sets a position of the imaging plane, wherein the imaging cross-section position setting unit includes a tissue extracting unit that extracts a specific tissue using an image acquired in advance by the imaging unit, a matching unit that performs a matching process on the specific tissue extracted by the tissue extracting unit using a template of the specific tissue, and a cross-section calculating unit that calculates a cross-section position including the specific tissue specified through the matching process.

Further, in a method for controlling an MRI apparatus according to the present invention, imaging of an imaging unit is controlled to perform a step of imaging a positioning image of a subject including a spine; a first imaging step of imaging a first cross section including the spine and extending along a longitudinal direction of the spine; and a second imaging step of imaging a second cross section in a direction of traversing the spine, and an automatic imaging position setting unit is controlled to perform an automatic positioning step of automatically setting a position of the cross section to be imaged in the second imaging step. Here, the automatic positioning step includes a tissue detection step of detecting a specific tissue of the spine using the positioning image or an image including the spine acquired in the first imaging step, a matching step of performing a matching process between a position of the specific tissue of the spine detected in the tissue detection step and a spine model, and a cross-section calculation step of calculating a position of the second cross section based upon the position of the specific tissue specified by matching with the spine model in the matching step.

Further, a program for auto-setting of an imaging plane according to the present invention causes a computer to execute the following steps of: receiving positioning images of a sagittal plane, an axial plane, and a coronal plane imaged by a magnetic resonance imaging apparatus; determining an image of the sagittal plane for determining an imaging cross-section position of the axial plane using at least one of the positioning images of the axial plane and the coronal plane; and determining the imaging cross-section position of the axial plane using the determined image of the sagittal plane, wherein the step of determining the imaging cross-section position of the axial plane includes: extracting a specific tissue from the determined image of the sagittal plane; performing a matching process on the extracted specific tissue using a deformation model of the specific tissue; and calculating the imaging cross-section position of the axial plane using a matching process result.

According to the present invention, a specific tissue is detected in advance, and a matching process is executed on the detected tissue, whereby it is possible to remarkably reduce the time required for the matching process. Further, since the matching process is performed using the limited number of adjustment parameters, it is possible to accurately specify a desired imaging plane without a possibility of falling into a local solution.

BRIEF DESCRIPTION OF DRAWINGS

FIGS. 9A and 9B are diagrams illustrating an example of a model used for the matching process;

FIGS. 15A and 15B are diagrams illustrating examples of filters used for preprocessing an image to be processed in determination of bilateral symmetry according to the second embodiment, wherein FIG. 15A illustrates a Gaussian filter and FIG. 15B illustrates a second-order differential filter;

FIGS. 16A and 16B are diagrams illustrating COR plane scout images before and after applying the filter process of FIGS. 15A and 15B, wherein FIG. 16A illustrates the COR plane scout images before the application and FIG. 16B illustrates the COR plane scout images after the application;

DESCRIPTION OF THE PREFERRED EMBODIMENTS

First, a configuration of an MRI apparatus common to various embodiments of the present invention and an embodiment of an imaging method using the same will be described with reference to FIGS. 1 to 3.

Configuration of Apparatus

Figure 1:
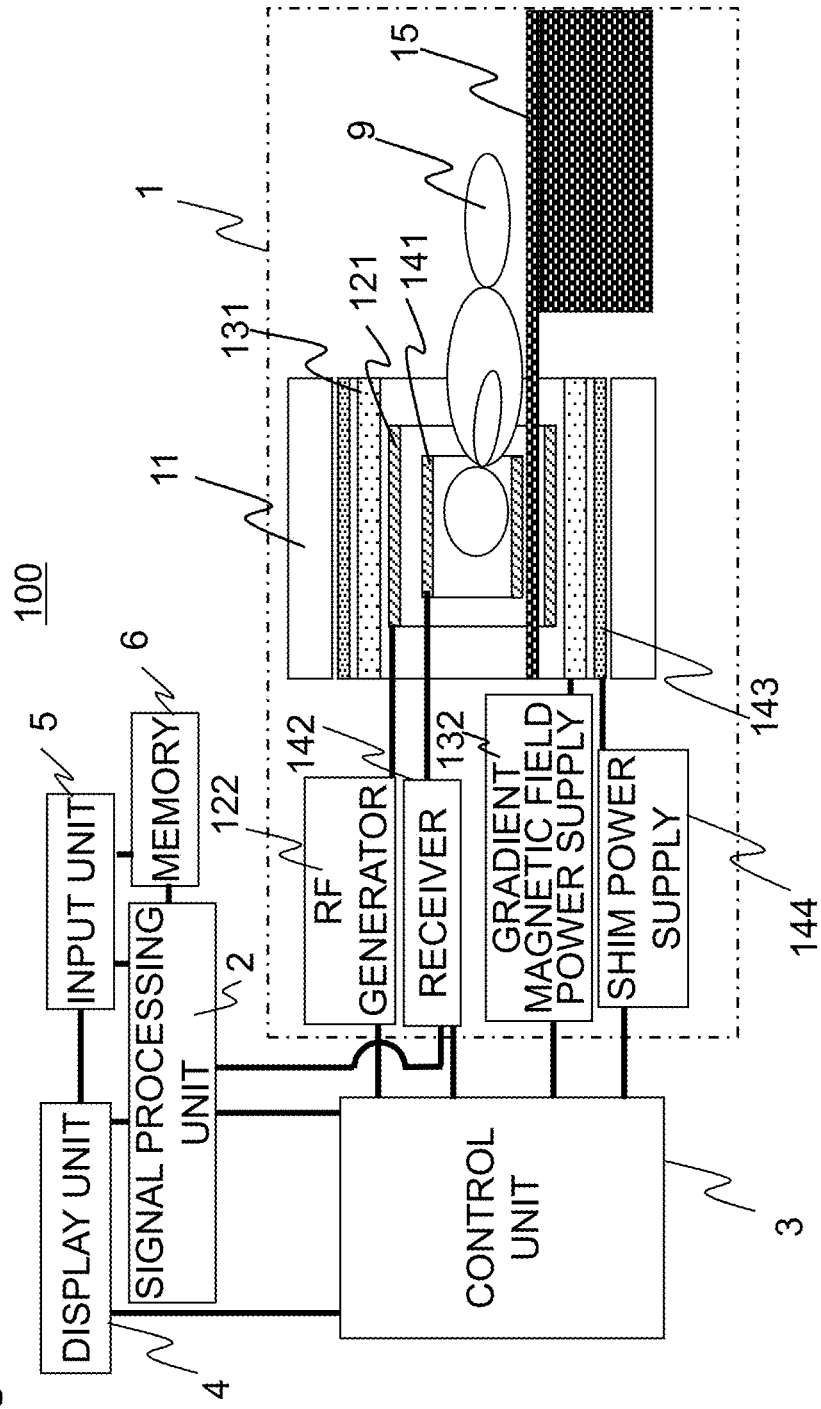
FIG. 1 is a diagram illustrating an overall configuration of an MRI apparatus to which the present invention is applied.
Figure 2:
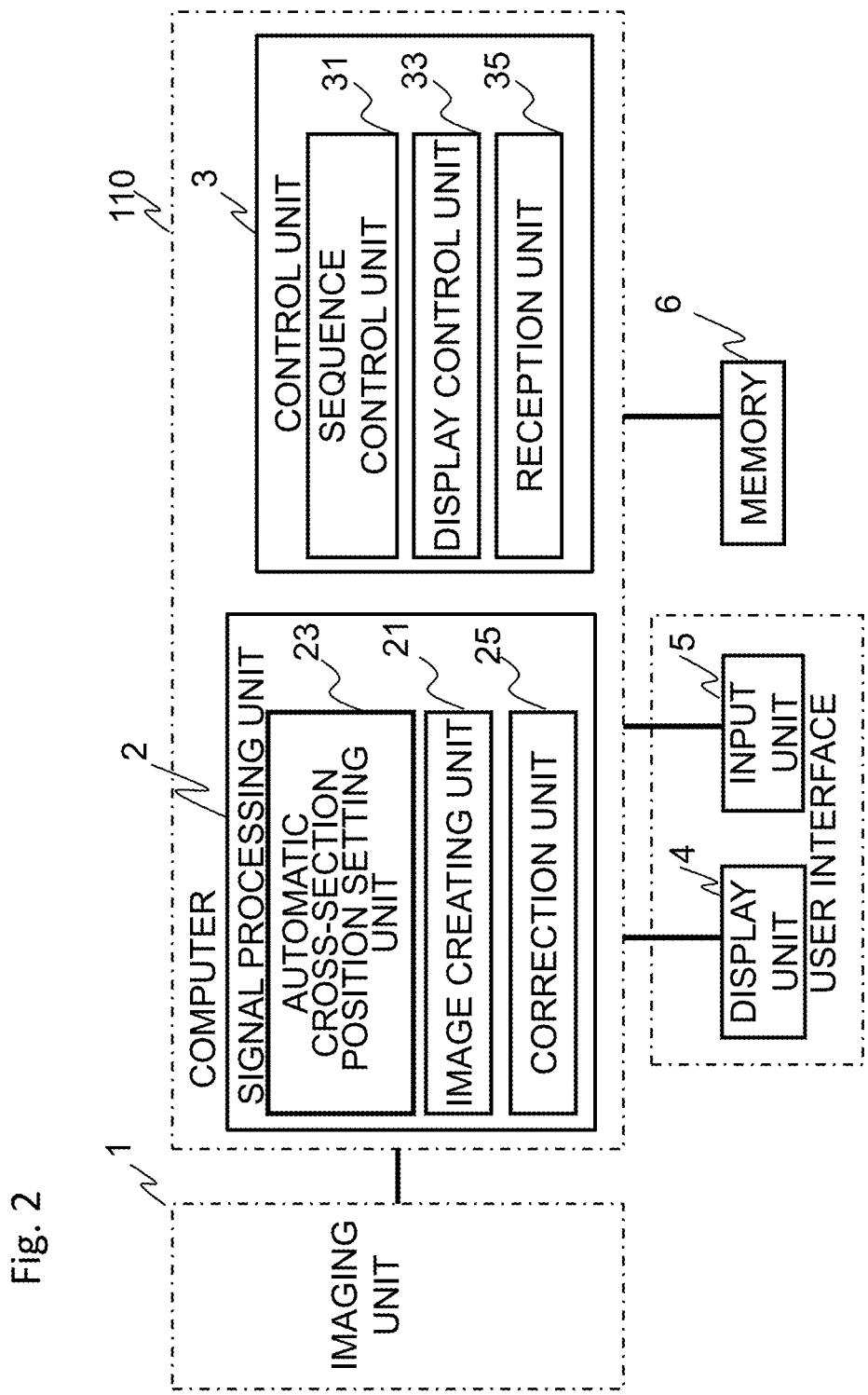
FIG. 2 is a diagram illustrating an overall configuration of an embodiment of the MRI apparatus.

FIG. 1 is an overall configuration diagram illustrating an imaging unit 1 of an MRI apparatus 100 according to the embodiment in detail, and FIG. 2 is a functional block diagram illustrating details of a signal processing unit 2 and a control unit 3. As illustrated in the diagram, the MRI apparatus 100 is roughly divided to include an imaging unit 1 that acquires a nuclear magnetic resonance signal; the signal processing unit 2 that performs a process such as creating an image using the nuclear magnetic resonance signal acquired by the imaging unit 1; and the control unit 3 that controls operations of the imaging unit 1 and the signal processing unit 2. The MRI apparatus 100 further includes a display unit 4 that displays a process result in the signal processing unit 2; a storage apparatus (a memory) 6 that holds the same process result; and an input unit 5 that receives an instruction from a user.

A configuration of the imaging unit 1 is the same as that of a general MRI apparatus, and the imaging unit 1 includes a magnet 11 that generates a uniform static magnetic field in a space (an examination space) in which a subject 9 is placed; a gradient magnetic field coil 131 that generates a gradient magnetic field; a gradient magnetic field power supply 132 that drives the gradient magnetic field coil 131; an RF coil 121 that irradiates the subject (a living body) 9 with a high frequency magnetic field pulse (hereinafter referred to as an RF pulse); a high frequency magnetic field generator 122 that drives the RF coil 121; an RF probe 141 that detects an echo signal (a nuclear magnetic resonance signal) generated from the subject 9; a receiver 142 that receives the echo signal detected by the RF probe 141; and a bed (a table) 15 on which the subject 9 is placed in a static magnetic field space generated by the magnet 11.

Further, when it is required to adjust uniformity of the static magnetic field, a shim coil 143 and a shim power supply 144 for driving the shim coil 143 are further included in some cases. The shim coil 143 is formed of a plurality of channels and generates an additional magnetic field that corrects non-uniformity of the static magnetic field by a current supplied from the shim power supply 144.

The signal processing unit 2 processes the echo signal received by the receiver 142 and performs computation such as image reconstruction, and the like. Therefore, as illustrated in FIG. 2, the signal processing unit 2 includes an image creating unit 21 that creates an image; an automatic imaging cross-section position setting unit 23 (hereinafter simply referred to as a cross-section position setting unit) that calculates an imaging cross-section position and presents the calculated imaging cross-section position to a user; a correction unit 25 that corrects the image created by the image creating unit 21 and the cross-section position calculated by the automatic cross-section position setting unit 23.

The control unit 3 controls operations of the imaging unit 1, the signal processing unit 2, and the like. Therefore, as illustrated in FIG. 2, the control unit 3 includes function units such as a sequence control unit 31, a display control unit 33, a reception unit 35 that receives condition setting and an instruction from a user, and the like. The sequence control unit 31 sends an instruction to the gradient magnetic field power supply 132 and the high frequency magnetic field generator 122 according to a predetermined pulse sequence, thereby not only generating a gradient magnetic field and a high frequency magnetic field, respectively, but also performing control required for imaging by the imaging unit 1 such as setting a nuclear magnetic resonance frequency serving as a reference of detection to the receiver 142. The display control unit 33 performs control for displaying the image created by the signal processing unit 2 and a display image including data, and the like stored in a storage apparatus 6 on the display unit 4, and performs control of a display screen. The reception unit 35 receives the condition setting and the instruction from the user to be inputted via the input unit 5.

In the embodiment illustrated in FIG. 2, functions of the signal processing unit 2 and the control unit 3 are realized by a computer 110. However, a part of the functions of the signal processing unit 2 and the control unit 3 may be realized by hardware other than the computer 110, for example, ASIC (Application Specific Integrated Circuit), FPGA (Field Programmable Gate Array), and the like.

In addition to the functions of the signal processing unit 2 and the control unit 3, the computer 110 controls a user interface such as the display unit 4, the input unit 5, and the like, and performs a user interface process of presenting a process result to a user and receiving an input from the user. Various kinds of data necessary for processes in the computer 110 are stored in the storage apparatus 6. The storage apparatus 6 may further store a process result by the signal processing unit 2, a detected signal itself, an imaging condition, and the like as necessary.

The imaging by the MRI apparatus 100 is performed not only by applying the RF pulse to the subject 9 through the RF coil 121 but also by applying the gradient magnetic field pulse for giving position information such as slice selection, phase encoding, and the like to the echo signal by the gradient magnetic field coil 131 under the control of the sequence control unit 31. A signal generated from the subject 9 by applying the RF pulse is received by the RF probe 141, and then the signal detected by the receiver 142 is sent to the signal processing unit 2 (the computer 110), whereby signal processes such as image reconstruction, and the like are performed therein.

In such imaging, it is possible to image an arbitrary imaging plane of the subject which is a target to be imaged by controlling the timing and intensity of the high frequency magnetic field and the gradient magnetic field set in the pulse sequence. In general, a position of the imaging plane in the subject which is the target to be imaged is determined and reflected on the pulse sequence, thereby imaging a desired imaging plane. The imaging cross-section position can be set by the user via the user interface, but the MRI apparatus 100 according to the embodiment is provided with a function (an automatic positioning function) of automatically setting the imaging cross-section position. In the example illustrated in FIG. 2, a case in which the automatic cross-section position setting unit 23 for realizing the positioning function is a part of the functions of the signal processing unit 2 is shown, however, alternatively, the function of the automatic cross-section position setting unit 23 can be also realized by an image processing apparatus separate from the signal processing unit 2 or by an independent computer.

Prior to a detailed description of the automatic cross-section position setting unit 23, a flow of the MR examination of the spine and setting of the imaging plane, to which the automatic positioning is applied, will be described with reference to FIGS. 3 and 4. FIG. 3 illustrates an example of a protocol (a protocol for determining an examination procedure) for performing the MR examination of the spine. FIG. 4 is a diagram illustrating a procedure of setting the imaging plane.

In the example illustrated in FIG. 3, first, imaging of a positioning image (hereinafter referred to as a scout image) for determining an imaging position is performed (S1). The scout image is an image of relatively low spatial resolution capable of imaging at a high speed, and normally obtains images having three-axis planes of an axial plane (an AX plane) orthogonal to a body axis; a coronal plane (a COR plane) which is parallel to the body axis and cuts a back side and an abdominal side of the subject; and a sagittal plane (a SAG plane) which is parallel to the body axis and cuts the right and left side of the subject, with respect to a wide region including an examination part of the subject. The images of these cross sections are 2D images, but 2D images of a plurality of slices may be acquired in some cases. The scout image is used to determine the imaging cross-section position of the subject in a subsequent main imaging.

After the imaging (S1) of the scout image, an image for calibration is acquired (S2). Imaging for calibration is imaging for obtaining data used for sensitivity correction of the RF probe 141 and is a 3D image.

Steps S1 and S2 are imaging as preparation before entering imaging (main imaging) for diagnosis, after which the main imaging is performed (S3). In the example illustrated in FIG. 3, the main imaging respectively performs imaging of a T1 weighted image and a T2 weighted image on the SAG plane and the AX plane (S3-1 to S3-4). Here, it is required to determine the respective positions of the SAG plane and the AX plane in the main imaging, and an automatic positioning process by the automatic cross-section position setting unit 23 is executed.

Next, an outline of imaging positioning using an anatomical feature of an examination part will be described with reference to FIG. 4 with a case in which the examination part is a spine or an intervertebral disk as an example. In this case, a case in which the positions of two imaging planes (the SAG plane and the AX plane) are determined from the scout image of the three-axis planes.

First, when determining the position of the SAG plane, an AX plane scout image (hereinafter referred to as an AX image) and a COR plane scout image (hereinafter referred to as a COR image) among a scout image 400 having three cross sections are used, an SAG plane 401 passing through an approximate center of the spine is determined based upon an anatomical feature of the examination part (for example, a spinal nerve in the case of the spine) (S41). Next, the imaging position of the AX plane is determined based upon an anatomical feature (for example, an intervertebral disk, a vertebral body, a vertebral arch, and the like) using the scout image of the determined SAG plane (hereinafter referred to as a SAG image) (S42). Further, in the scout image of the SAG plane for determining the AX plane, when the spinal nerve, which is the anatomical feature, is parallel to a coordinate axis of the image, as illustrated in a rectangle of a single dotted line in the drawing, a SAG image including the spinal nerve from among the SAG images of the plurality of slices is used as a SAG image for determining the position of the AX plane. However, in the scout image, since the spine is not necessarily limited to being parallel to the coordinate axis of the COR image, in this case, the SAG image of the plurality of slices may be used; the SAG image including the spinal nerve may be cut out by an interpolation process; and the SAG image, which is cut out by the interpolation process, may be used for setting the position of the AX plane, or alternatively, an image of the slice including the spinal nerve the most may be used as the SAG image for the position setting of the AX plane.

The imaging positions of the SAG plane and the AX plane in the main imaging are determined by the above-described procedure.

Here, when the anatomical feature used at the time of setting the imaging position of the AX plane is, for example, the intervertebral disk, in the case of the normal spine, the AX plane can be set for each intervertebral disk included in the examination part, whereas there also exists a case in which the position cannot be specified only with a feature such as damage to the intervertebral disk, and the like. Further, when the scout image used for the positioning is an image including a part of the spine, it is difficult to accurately grasp the number of the intervertebral disk, that is, the position of the spine.

When executing the imaging method as described above, the MRI apparatus according to the embodiment is characterized in that automatic imaging position setting (the automatic positioning) is realized with a small calculation amount, that is, at a high speed and with high accuracy by combining a predetermined tissue extracting method and a matching method. Hereinafter, an embodiment of a specific method will be described.

First Embodiment

In the embodiment, tissue extraction of a specific tissue using an anatomical feature is performed using the scout image; a matching process using a template (also referred to as a model) of the specific tissue is performed on the extracted specific tissue; a position of the specific tissue is specified; and an imaging position is calculated.

Figure 5:
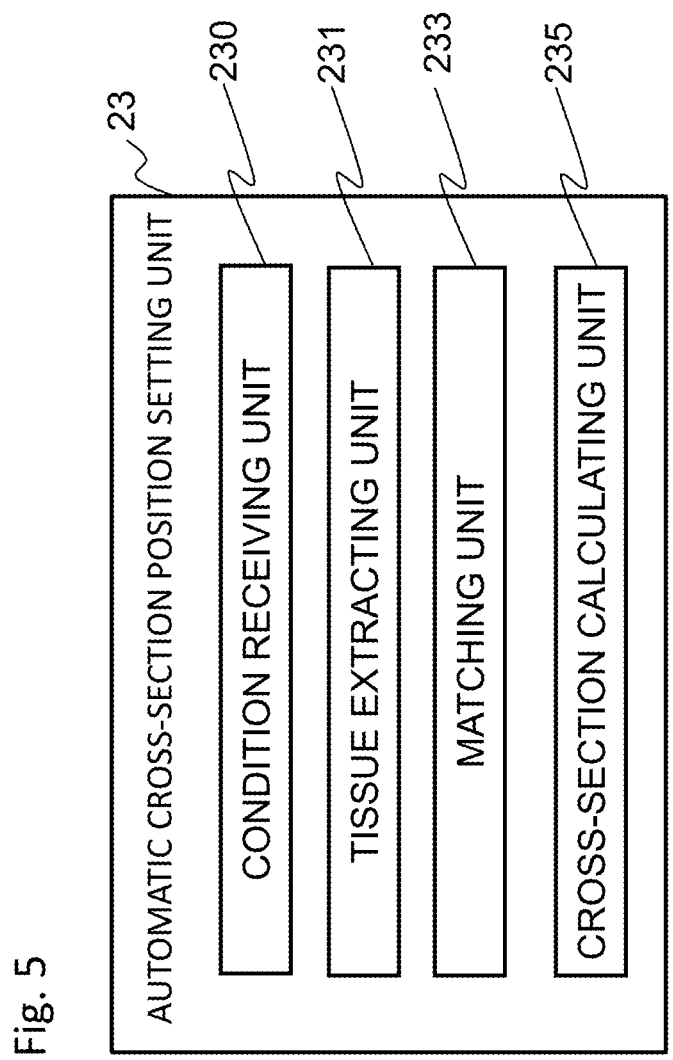
FIG. 5 is a functional block diagram of an automatic cross-section position setting unit according to a first embodiment.

First, an outline of a function of the automatic cross-section position setting unit 23 according to the embodiment will be described with reference to a block diagram of FIG. 5. As illustrated in FIG. 5, the automatic cross-section position setting unit 23 includes a condition receiving unit 230, a tissue extracting unit 231, a matching unit 233, and a cross-section calculating unit 235. The condition receiving unit 230 receives a condition inputted by the user via the user interface and a condition required for the automatic positioning process set in the control unit 3. For example, as illustrated in FIG. 3, information of an examination protocol that determines what kind of imaging is to be performed on which part is given to each unit of the automatic cross-section position setting unit 23 via the condition receiving unit 230.

The tissue extracting unit 231 detects a specific tissue (for example, the intervertebral disk or the vertebral body) by an object extraction method using the anatomical feature of the tissue. Various methods (algorithms) are known for the object extraction method, and, in the embodiment, the specific tissue is extracted by using a machine learning algorithm learned by learning data of the specific tissue, and a position thereof is detected. The matching unit 233 performs the matching process on the detected specific tissue by using a model of the specific tissue. The model may use a standard shape model of the specific tissue, but in the embodiment, a model (a deformation model) which is deformable under a specific constraint is used.

Figure 6:
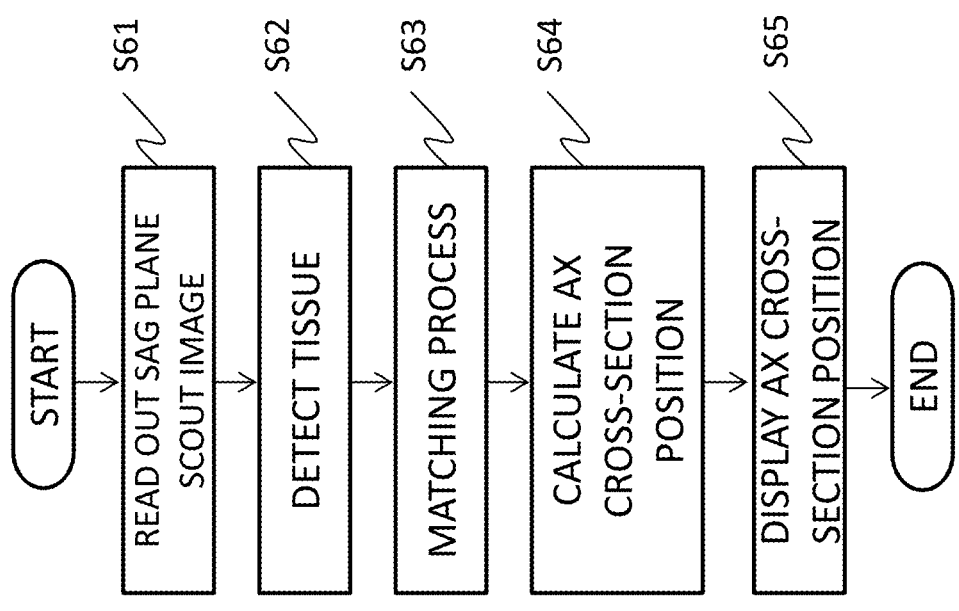
FIG. 6 is a flowchart illustrating a procedure of automatic positioning according to the first embodiment.

Next, an automatic positioning procedure by the automatic cross-section position setting unit 23 will be described. A case in which as a prerequisite for the automatic positioning, the scout image of the three-axis planes (FIG. 4: 400) is acquired and stored in the storage apparatus 6, and the position of the AX plane (one or a plurality of cross-section positions) of the main imaging is automatically set from the scout image of the SAG plane will be described as an example. FIG. 6 schematically illustrates a process thereof.

S61: Image Readout

First, the SAG image including the spine is read out from the storage apparatus 6. When there exists an image of a plurality of slices, the SAG image including the spine is selected by a simple feature extraction method from the COR image. Alternatively, the SAG image including the spine may be created by the interpolation process using the plurality of images.

S62: Tissue Detection

Next, the tissue extracting unit 231 searches for the specific tissue, for example, the intervertebral disk using, for example, the object extraction method by machine learning. A well-known machine learning algorithm can be adopted for the object extraction method by the machine learning. Here, a case in which the tissue extraction is performed by an adaptive booting method (hereinafter referred to as an AdaBoost method) which is one of the object extraction methods will be described.

Figure 7:
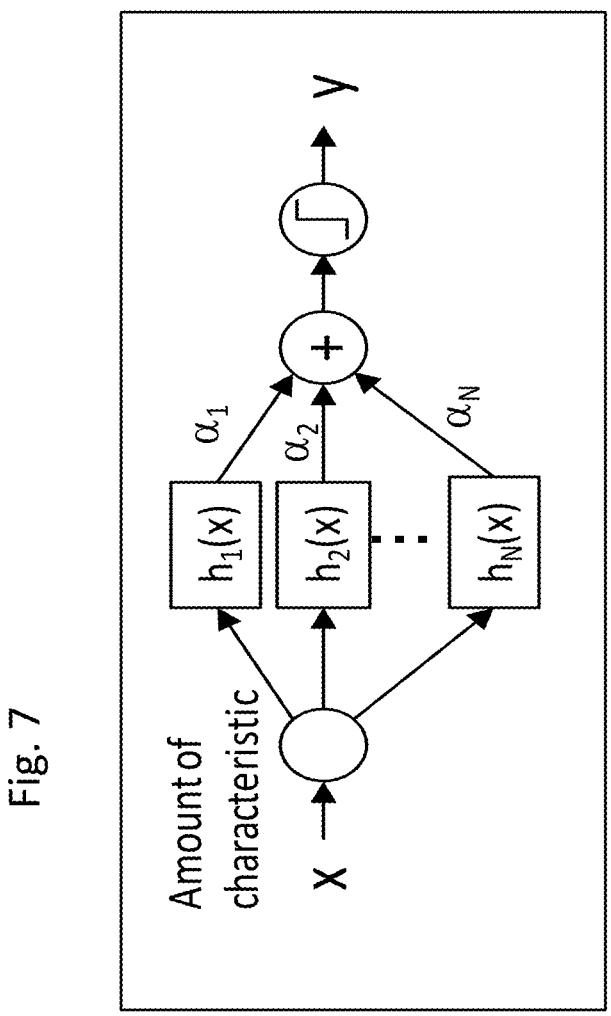
FIG. 7 is a diagram illustrating an outline of an AdaBoost method used for the automatic positioning according to the first embodiment.

In the AdaBoost method, as illustrated in FIG. 7, the number N of a weak discriminator to be used is set first; each discriminator hi(x) (i is 1, 2, . . . N, hereinafter the same) discriminates a correct answer and an incorrect answer by using input data x and output data y whose correct and incorrect answers are known in advance; and when the results are combined with each other, a weight αi of the weak discriminator capable of being separated most accurately is calculated. After preparing the weak discriminator learned as described above, each weak discriminator hi (x) determines the correct answer or incorrect answer from a feature amount of the input data x, and the final discrimination is determined by a weighted majority decision of the weak discriminator.

An embodiment in which a weight of the weak discriminator is acquired by learning using the SAG image actually including the spine will be described. In the embodiment, correct answer data in which only the intervertebral disk is extracted and incorrect answer data in which the intervertebral disk is removed are prepared as learning data. At this time, in order to increase the number of learning data, an original image is rotated at −10, −5, 0, 5, and 10 degrees, and then the correct answer data and the incorrect answer data are prepared for each rotated image. Further, as the image feature amount (that is, input data) processed by the weak discriminator, LBP (Local Binary Patterns) is used. The LBP divides an image, binarizes a 3×3 region within the divided image, converts one in which the binarized data are arranged in order into a decimal number, and applies the decimal number to the whole divided image, thereby being used as a histogram of the decimal number. Further, the feature amount includes well-known feature amount such as Haar-Like, HOG, and the like in addition to the LBP, and any of the feature amounts can be applied thereto, however, the LBP feature amount is desirable because the LBP feature amount is robust against a contrast change caused by sensitivity unevenness (robustness is high) and has a short calculation time. The tissue extracting unit 231 outputs detection information on the detected intervertebral disk from the output data y obtained by such the AdaBoost method. The detection information includes either one of a position of the SAG image, a size, and a distance between the intervertebral disks.

S63: Matching Process

The matching unit 233 performs matching by using a tissue model based upon the detection information of the specific tissue (the intervertebral disk) detected by the tissue extracting unit 231.

In the matching, various kinds of methods such as an appearance-based method, a feature-based method, and the like and algorithms thereof have been developed, and an arbitrary method can be selected depending on the shape of the target tissue and the feature thereof. In the embodiment, a matching process (hereinafter referred to as an ASM method) by an Active Shape model (an ASM method) which is one of the feature-based matching methods is adopted. That is, the matching process using a deformation model obtained by deforming a model of the specific tissue under a fixed constraint (a statistical constraint) is performed.

The ASM is formed of a plurality of sample image groups by a statistical process and is formed by a standard model shape and a parameter for deforming a model shape within a range of an individual difference. Since the ASM method uses a model including a parameter for deformation as a feature, the matching accuracy is higher in comparison with a case in which a fixed shape model is used, and since a deformation range is limited to the range of the individual difference between samples, there exists an advantage in that a matched shape does not largely deviate from an actual shape.

The matching process includes determination of an initial position at which the matching with the model is performed, determination of a matching range, and deformation of the model based upon the detected position of the intervertebral disk. Hereinafter, an embodiment in which the ASM method is actually applied by using a spine model (a sample image) will be described.

Determination of Initial Position

Figure 8:
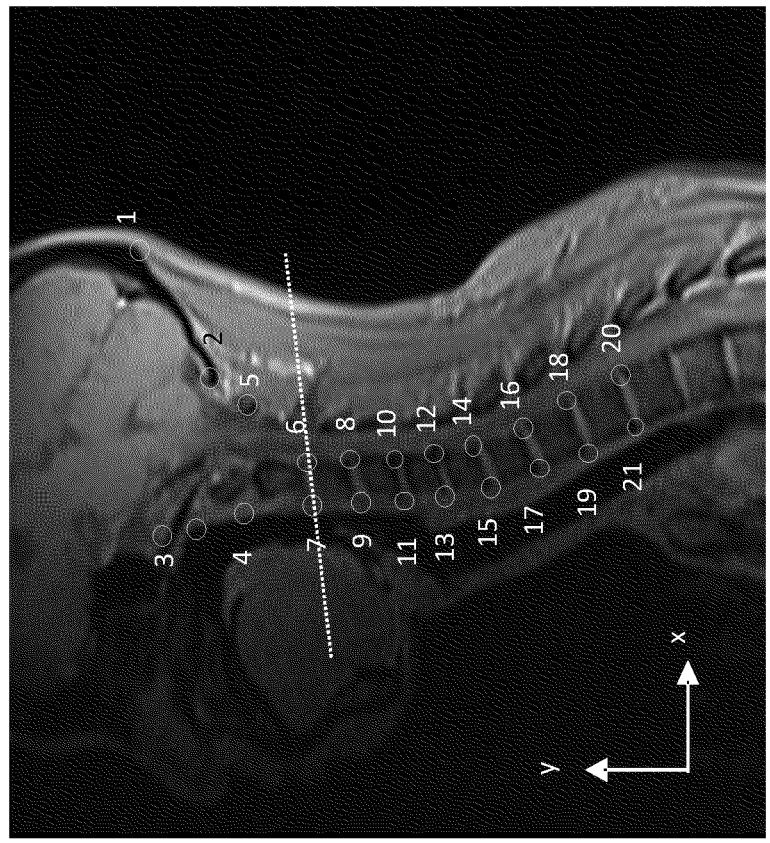
FIG. 8 is a diagram illustrating a matching process according to the first embodiment.

First, in a plurality of sample images (for example, 100 examples), coordinates of a plurality of positions corresponding to predetermined features are acquired. Specifically, coordinates of mark points from the first to the 21st illustrated in FIG. 8 are acquired. Next, after the mark point coordinates are moved in parallel so that a center of a line connecting the sixth and seventh mark points corresponding to the second vertebral body and the third vertebral body becomes an origin point, a size is standardized by dividing each mark coordinate by a distance between the sixth mark point and the seventh mark point.

Deformation of Model

Next, mark points of other samples are aligned with reference to the mark point of the first sample image. Specifically, if the total number of mark points is N, rotation and an enlargement and reduction process of coordinates (xk, n, yk, n) of marks of the k-th sample images (k is an integer from 2 to N) are performed at an enlargement and reduction coefficient s and a rotation angle θ in which an evaluation function E represented by Equation (1) becomes minimum.

$$E = \sum_{n=1}^{N}\left(\begin{pmatrix}x_{1,n}\\y_{1,n}\end{pmatrix} - s\begin{pmatrix}\cos\theta & -\sin\theta\\\sin\theta & \cos\theta\end{pmatrix}\begin{pmatrix}x_{k,n}\\y_{k,n}\end{pmatrix}\right) \quad (1)$$

Next, an average value between the samples is calculated with respect to the marks obtained by the above-described enlargement and reduction process. The average value can be calculated by Equation (3) when the coordinates of the marks are represented by a vector x of Equation (2).

$$x_k = (x_{k,1}, y_{k,1}, x_{k,2}, y_{k,2}, \ldots, x_{k,N}, y_{k,N}) \quad (2)$$

$$\bar{x} = \frac{1}{M}\sum_{k=1}^{M} x_k \quad (3)$$

In Equation (3), M is the number of samples (100 in the embodiment), and the obtained average value between the samples represents a standard shape of the model.

Next, a deformation parameter for deforming the standard shape is calculated. Therefore, first, a difference dxk between the average value between the samples and each sample mark is obtained, and then a variance-covariance matrix S is calculated by the following Equation (4).

$$S = \frac{1}{M}\sum_{k=1}^{M} dx_k dx_k^T \quad (4)$$

When an eigenvector of the matrix S is defined as P, the ASM can be represented by Equation (5).

$$x = \bar{x} + bP \quad (5)$$

The eigenvector P is a parameter for deforming the standard shape of the model and represents a change tendency between the individual differences. b is a coefficient set according to a variation in the individual difference. Generally, the larger an eigenvalue λn is, the larger the variation in the individual difference in a direction of a corresponding eigenvector Pn is. Accordingly, for example, the coefficient b is set within a range of Equation (6).

$$-3\sqrt{\lambda_n} \leq b_n \leq 3\sqrt{\lambda_n} \quad (6)$$

FIGS. 9A and 9B are diagrams, which are two dimensionally plotted, illustrating a standard shape (a) of the ASM prepared by the embodiment and a model shape (b) obtained by deforming the standard shape by the coefficient b.

Matching Process

Next, a flow of a matching process using the ASM determined by the above-described standard shape and the deformation parameter will be described with reference to FIG. 10.

As a prerequisite, the position and size of the intervertebral disk detected by the AdaBoost method are respectively defined as $(xd_i, yd_i)$ and $w_i$ (i=1, . . . , Nd). Here, as the "I" is smaller, the intervertebral disk is rearranged to become an intervertebral disk closer to a parietal side. The standard shape of the ASM (Equation 3) sets a size of a spine of a target image to be equal. The size of the spine of the target image is calculated by integrating the average value of the detected intervertebral disk size. Here, the calculated coordinates of the standard shape (coordinates from the first to 21st marks illustrated in FIG. 8) are defined as $(xd_j, yd_j)$ (j=1, . . . , 21).

First, in the target image (the SAG image in the embodiment), a position of a brain bottom part to be a reference of a height is extracted (S631). Specifically, an upper edge part of the back side is extracted, and a skull region is extracted by a region expansion method starting from a point that is close to an edge point and has a low pixel value as a starting point. A point y0 on the lowest limb side of the extracted region is defined as the position of the brain bottom part.

Next, an intervertebral disk between the second vertebral body and the third vertebral body is extracted (S632). It is expected that the intervertebral disk between the second vertebral body and the third vertebral body is an intervertebral disk $(xd_1, yd_1)$ detected at the top side of the head by the AdaBoost method, however, since it is also assumed that the detection of the intervertebral disk fails, here, the embodiment uses a principle that the intervertebral disk between the second vertebral body and the third vertebral body is anatomically positioned below the brain bottom part, and the intervertebral disk is searched again by a simple method based upon a pixel value. That is, coordinates (coordinates of positions along a vertical axis) y1 and y2 are obtained by the following Equation (7).

$$\begin{cases} y1 = y0 - 0.25(yo_2 - 0.5(yo_6 + yo_7)) \\ \quad y2 = 0.5(yd_1 + yd_2) \end{cases} \quad (7)$$

Next, the intervertebral disk positions $(xd_i, yd_i)$ detected by the AdaBoost method are fitted by a quadratic function, and pixel values on a quadratic curve between y1 and y2 are extracted. Since the luminance of the intervertebral disk is high and the luminance of the vertebral body is low on the SAG image, a region that continuously exceeds a threshold value is extracted while setting the maximum pixel value× 0.8 as the threshold value, and a center position of the obtained region is set to a center position $(xd_o, yd_o)$ of the intervertebral disk between the second vertebral body and the third vertebral body. Here, when there is a plurality of regions exceeding the threshold value, a center position of a region close to y1 is set to the position $(xd_o, yd_o)$ of the intervertebral disk between the second vertebral body and the third vertebral body. y1 is an upper limit value at which the intervertebral disk between the second vertebral body and the third vertebral body can exist; a distance from the brain bottom part to the intervertebral disk between the second vertebral body and the third vertebral body in the standard shape model is set as a reference distance; and the y1 is defined as a position of one quarter of the reference distance from the brain bottom position of the target image. Further, y2 is a center value of two intervertebral disks which are close to the head top side among the intervertebral disks extracted by the AdaBoost method, and at least one intervertebral disk searched at the head top side is included between the y1 and the y2. In other words, when there is no detection omission, $(xd_o, yd_o)=(xd_1, yd_1)$ becomes the intervertebral disk between the second vertebral body and the third vertebral body, and when the detection omission occurs, a point above $(xd_1, yd_1)$ is extracted as the intervertebral disk between the second vertebral body and the third vertebral body.

Next, a candidate position of a matching position is calculated (S633). Therefore, first, while setting the position $(xd_o, yd_o)$ of the intervertebral disk between the second vertebral body and the third vertebral body as the starting point, a pixel value on a straight line obtained by sequentially connecting the center positions of the intervertebral disks detected by the AdaBoost method from the head top side is plotted. Here, a length between the intervertebral disks of the standard model is defined as $L_k$ (k=1, . . . , 7), and a pixel value extracted at an $L_k$ interval in the plotted image value is defined as $SI(L_k)$. A coefficient for adjusting the size of the model is defined as a, and $a_{opt}$ in which the total value of pixel values SI $(a \cdot L_k)$ becomes maximum is obtained. Next, coordinates $(xd_k', yd_k')$ of the pixel value SI $(a_{opt} \cdot L_k)$ are acquired, and the acquired coordinates are set as the candidate position of the intervertebral disk part in the matching process. Further, the edge of the brain bottom region extracted in S31 is extracted and the lowest limb side point is defined as $(xb_2, yb_2)$; and an edge point closest to a point advancing from $(xb_2, yb_2)$ toward a main component direction of the brain bottom region only by a distance d represented by Equation (8) is defined as $(xb_1, yb_1)$. $(xb_1, yb_1)$ and $(xb_2, yb_2)$ are defined as the candidate positions of the brain bottom part in the matching process.

$$d = a_{opt} \sqrt{(xo_1 - xo_2)^2 + (yo_1 - yo_2)^2} \quad (8)$$

The model is deformed, and the matching process is performed by using the above-described candidate position of the matching position (S634). Therefore, difference values $(d_x b_k, d_y b_k)$ between the intervertebral disk part of the standard shape model and the candidate position, and difference values $(d_x d_k, d_y d_k)$ between the brain bottom part of the standard shape model and the candidate position are calculated by Equations (9) and (10), and a difference vector dv, which is represented by Equation (11), between the standard shape model and the candidate position is obtained.

$$\begin{pmatrix} dxd_k \\ dyd_k \end{pmatrix} = \begin{pmatrix} xd_k' - (0.5(xo_{k+5} + xo_{k+6}) + xdo) \\ yd_k' - (0.5(yo_{k+5} + yo_{k+6}) + ydo) \end{pmatrix} \quad (9)$$

$(k = 1, \ldots, 7)$ $$\begin{pmatrix} dxb_k \\ dyb_k \end{pmatrix} = \begin{pmatrix} xb_k - (xo_k + xdo) \\ yb_k - (yo_k + ydo) \end{pmatrix} \quad (10)$$

$(k = 1, 2)$ $$dv = (dxb_1, dyb_1, dxb_2, dyb_2, 0, 0, 0, 0, 0, 0, dxd_1, dyd_1, dxd_1, \\ dyd_1, dxd_2, dyd_2, dxd_2, dyd_2, \ldots, dxd_7, dyd_7, dxd_7, dyd_7) \quad (11)$$

Here, since points corresponding to the third to fifth mark points do not affect the matching, the difference is set to 0. Since the intervertebral disk is represented by points at opposite ends in the model, the difference value calculated by Equation (9) is respectively applied to the points at opposite ends. According to Equation (5), a deformation parameter b in the matching process is represented by Equation (12).

$$b = P^T dv \quad (12)$$

When the deformation parameter b is determined, the coordinates of the model after the matching can be calculated by using Equation (5).

Step S63 illustrated in FIG. 6 is completed by the above-described processes (S631 to S634), and the position of the intervertebral disk in the target image (the SAG image) is specified.

[S64: Calculation of Cross-Section Position

Figure 10:
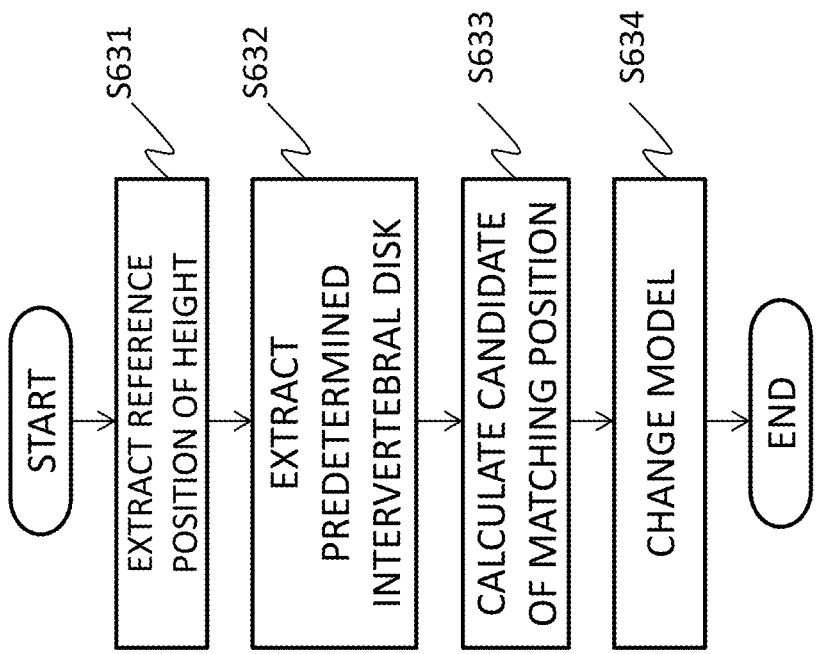
FIG. 10 is a flowchart illustrating a procedure of the matching process.

The cross-section calculating unit 235 calculates an AX cross section passing through each intervertebral disk by using the position of the intervertebral disk in the SAG image calculated by the matching processes (S3, FIG. 10: S631 to S634). Specifically, a cross section including the straight line passing through the points at opposite ends of the intervertebral disk and orthogonal to the SAG image is determined.

S65: Display of Recommended Cross-Section Position

Figure 11:
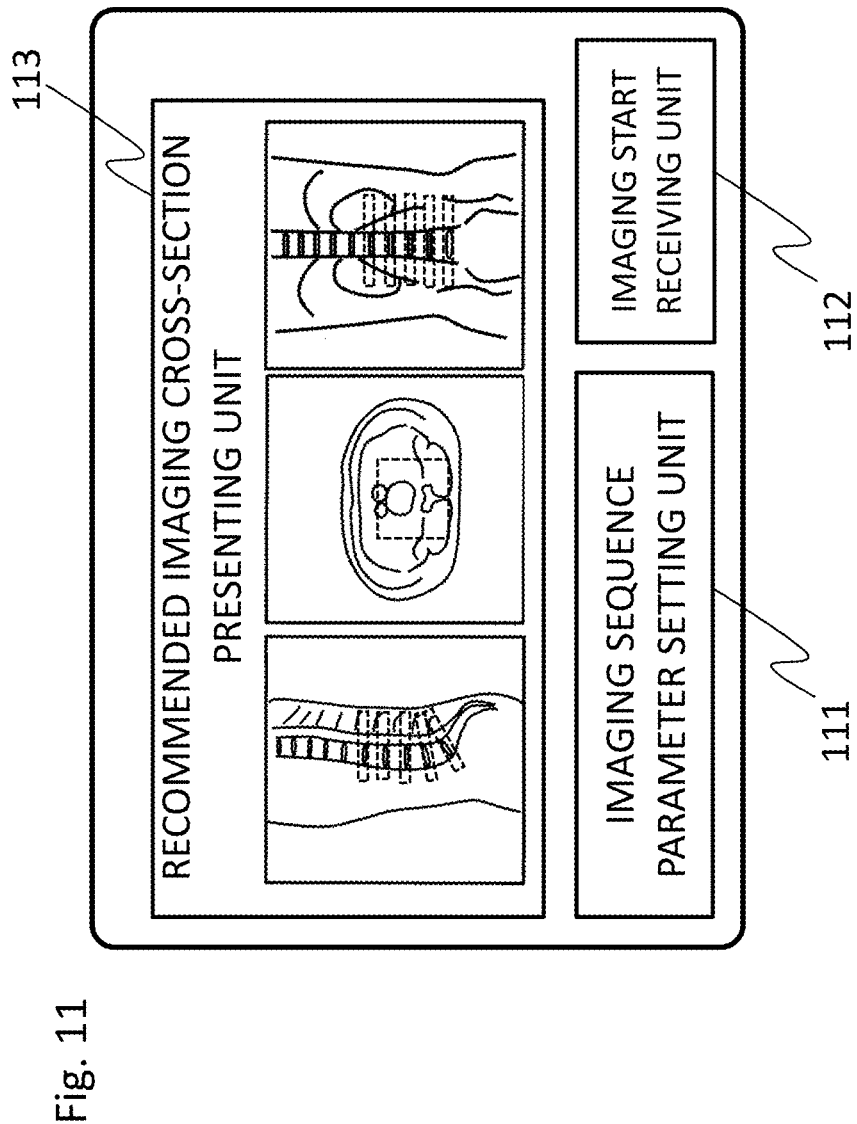
FIG. 11 is a diagram illustrating a display example of an imaging cross-section position determined by the automatic positioning.

The cross section determined by the automatic cross-section position setting unit 23 in steps S61 to S64 is displayed on a display screen of the display apparatus 4. A display example is illustrated in FIG. 11. The display screen is a screen on which a UI for setting the imaging condition, and the like is displayed, and an imaging sequence parameter setting unit 111, an imaging start receiving unit 112 that receives an instruction to start the main imaging, and a recommended imaging cross-section presenting unit 113 are provided in a display area of the display screen. The cross section determined by the automatic cross-section position setting unit 23 is displayed on the recommended imaging cross-section presenting unit 113. In the diagram, an image that is superimposed with a mark (in this case, a quadrangle indicated by a dotted line) that indicates an imaging cross-section position of three-axis-planes diagram of the SAG, the AX and the COR is presented. The user confirms the recommended imaging cross-section position by the display, and then sends an instruction to start the main imaging to the control unit 3 via the imaging start receiving unit 112. Although not illustrated in FIG. 11, for example, a GUI having a function of moving, rotating, deleting, and adding a mark may be added, and a change by the user may be received on the recommended imaging plane.

According to the embodiment, first, the tissue extraction using the anatomical feature of the specific tissue of the spine is performed using the positioning image (the scout image); after calculating the coordinates of the specific tissue, the matching process between the position of the specific tissue and the model is performed; and the calculation of the tissue position can be performed with high accuracy in a relatively short time by determining the position of the extracted tissue in the spine and correcting erroneous recognition which may occur in the tissue extraction. The cross section including the tissue to be examined can be determined with high accuracy by using the position calculated as described above.

Further, in the embodiment, an example of performing the matching process based upon the brain bottom part as a reference has been described, however, alternatively, a tissue as an appropriate reference is arbitrary in such a manner that a sacral side is set as a reference or a tissue other than the spine existing near the spine and an intervertebral disk at a position corresponding thereto are set as a reference. For example, a plurality of models including an appropriate reference in relation to the examination part may be prepared; the examination part may be received by the condition receiving unit 230; and an appropriate model may be automatically selected according to the received examination part.

Modified Example of First Embodiment

In the first embodiment, the imaging position is set by using the scout image, however, alternatively, in the embodiment, when a plurality of kinds of imaging are continuously executed in the main imaging, an imaging position in the subsequent imaging may be set using the image acquired in the preceding imaging.

Figure 3:
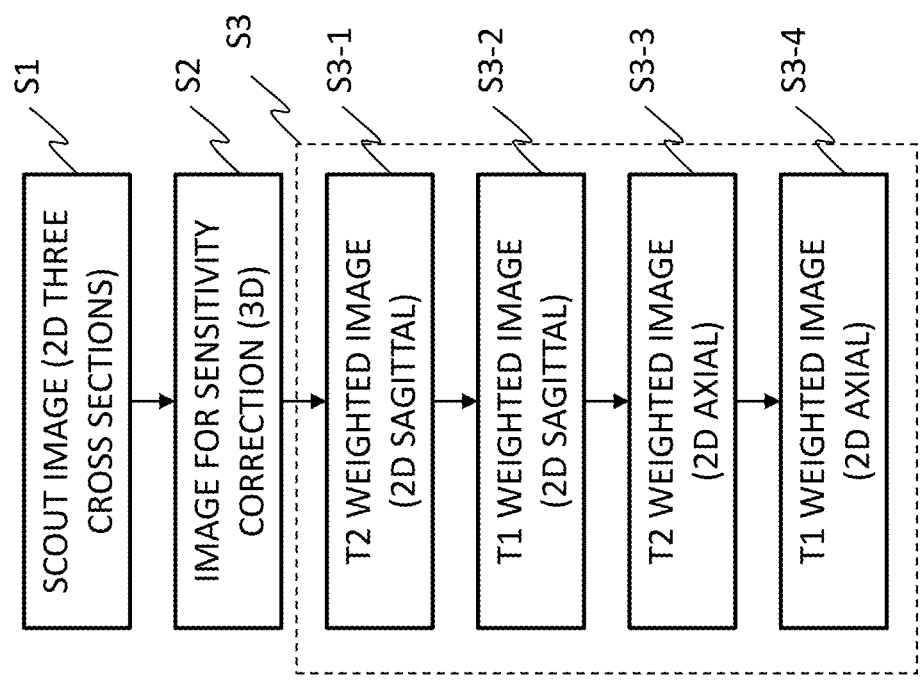
FIG. 3 is a diagram illustrating an example of a spinal MR examination protocol using the MRI apparatus.
Figure 4:
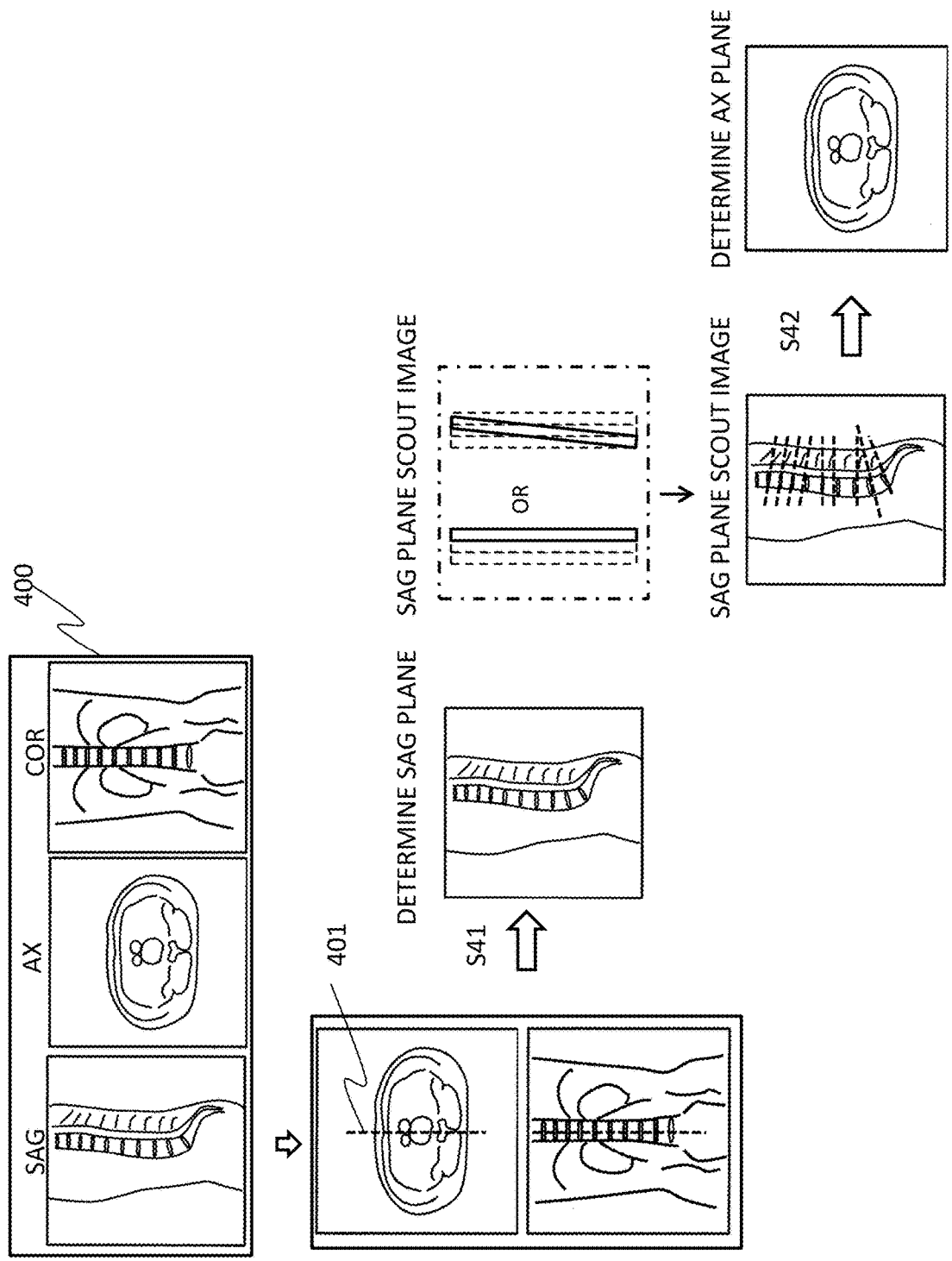
FIG. 4 is a diagram illustrating an outline of an imaging positioning method in the related art.

For example, when the imaging is performed according to the examination protocol illustrated in FIG. 3, the imaging (S3-1, S3-2) of the SAG plane (a first cross section) to be executed first and second in the main imaging determines the imaging position of the SAG plane using the scout images of the COR plane and the AX plane; and the imaging (S3-3 and S3-4) of the AX plane (a second cross section) to be executed third and fourth determines the imaging position using the image of the SAG plane acquired in the main imaging. The method for determining the imaging position is the same as that of the first embodiment, and according to the procedures (steps S61 to S64) illustrated in FIG. 6, the tissue extraction and the matching process are performed, thereby determining the imaging position of the AX plane.

According to the modified example, since the imaging position of the AX plane is determined after imaging the SAG plane, in comparison with the first embodiment, the examination time takes longer as much as the time required for determining the imaging position. However, since an image having a higher resolution than that of the scout image is used, the anatomical feature (the intervertebral disk, and the like) can be extracted more accurately in the tissue extraction, and the accuracy of the matching process thereafter and the accuracy of the imaging positioning can be improved.

Further, when two kinds of imaging (S3-1 and S3-2) are performed on the SAG plane, the examination can be performed without extending the examination time by calculating the cross-section position of the AX plane in parallel with the next imaging S3-2 using the image acquired in the first imaging S3-1.

Second Embodiment

In the first embodiment and in the modified example thereof, a case in which the tissue detection and the matching process are performed by using the SAG image for positioning or the image of the SAG plane (the first cross section) obtained in the main imaging, and the imaging position of the AX plane (the second cross section) is determined has been descried, however, the MRI apparatus according to the embodiment reconstructs the image of the SAG plane used for determining the imaging position of the AX plane using the AX image for positioning and the COR image. That is, the imaging cross-section position setting unit 23 further includes a median plane detecting unit 237 that extracts the anatomical feature of the image acquired by positioning imaging and detects a median plane, and reconstructs and uses an image of a position of the median plane detected by the median plane detecting unit 237 as the image of the first cross section used for setting the imaging position of the second cross section.

Figure 12:
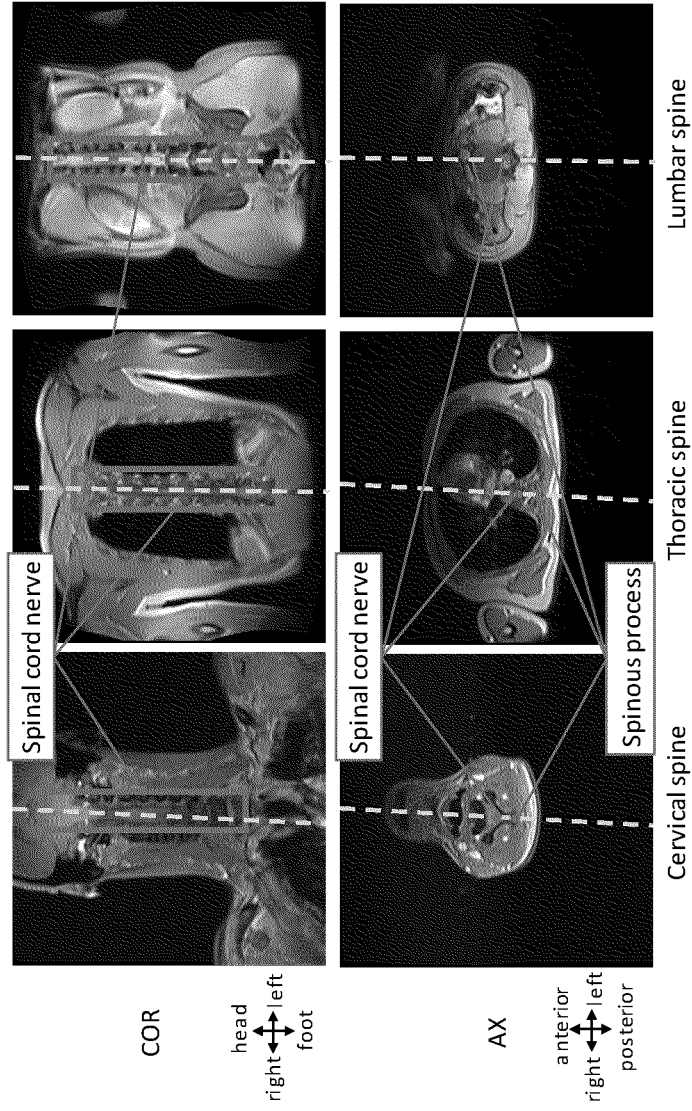
FIG. 12 is a diagram illustrating an AX image and a COR image used for the automatic positioning of a SAG plane according to the first embodiment.

FIG. 12 illustrates the COR image (an upper view) and the AX image (a lower view) at respective parts of a cervical spine, a thoracic spine, and a lumbar spine which are target images to be processed of the median plane detecting unit 237. Ideally, it is desirable that the SAG plane passes through the center of the spinal nerve and is symmetric with respect to the human body, however, as illustrated in the diagram, a direction of the spine is not necessarily parallel to the coordinate axis of the image in the COR image and the AX image. Therefore, in the automatic cross-section position setting of the SAG image according to the embodiment, while paying attention to a fact that an anatomical structure in the vicinity of the vertebral body and the spinal nerve becomes a bilateral symmetry structure, a plane in which a bilateral symmetry index in a region of interest becomes maximum is extracted.

Specifically, for each part, in the COR plane scout image, the SAG plane is set to an inclination along the spinal nerve, and in the AX plane scout image, the SAG plane is set to an inclination that passes through the spinal nerve and a spinous process.

Figure 13:
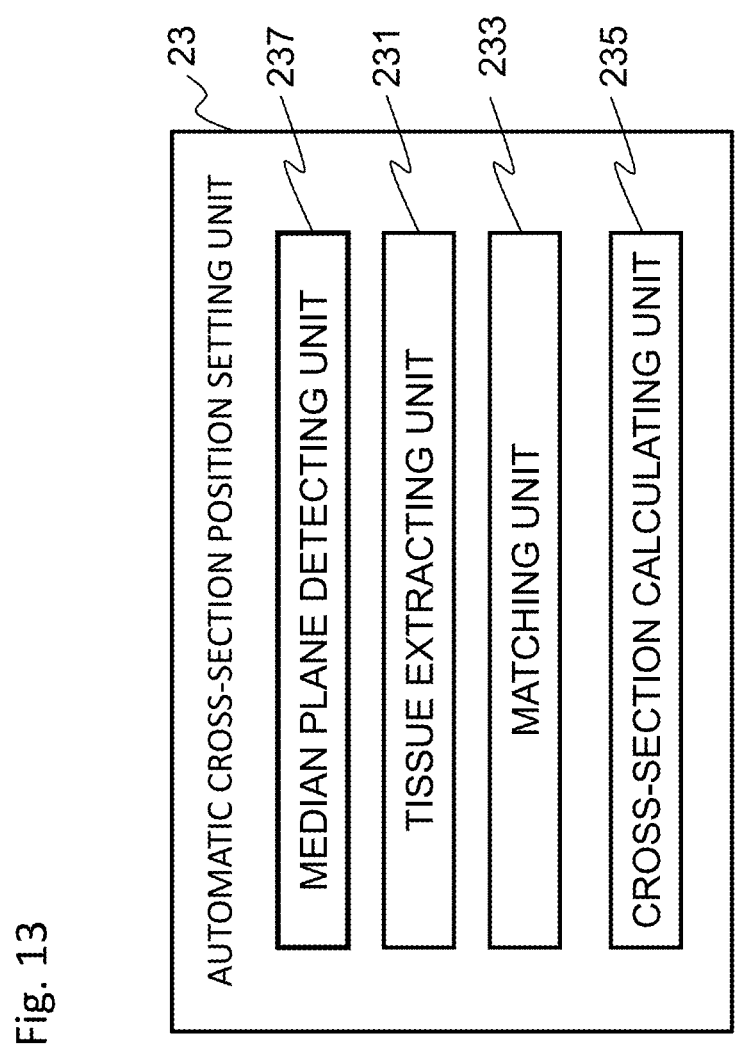
FIG. 13 is a functional block diagram of an automatic cross-section position setting unit according to a second embodiment.

FIG. 13 illustrates a configuration of the automatic cross-section position setting unit 23. In FIG. 13, the same elements as those of FIG. 5 are denoted by the same reference signs, and a redundant description thereof will be omitted. The automatic cross-section position setting unit 23 according to the embodiment is characterized by including the median plane detecting unit (an anatomical feature structure extraction unit) 237 in addition to the tissue extracting unit 231, the matching processing unit 233, and the imaging cross-section calculating unit 235. Even in the embodiment, since the method for the tissue detection and the matching process is the same as that of the first embodiment, hereinafter, an embodiment of a method for calculating the median plane image will be described by centering on a function of the median plane detecting unit 237.

Figure 14:
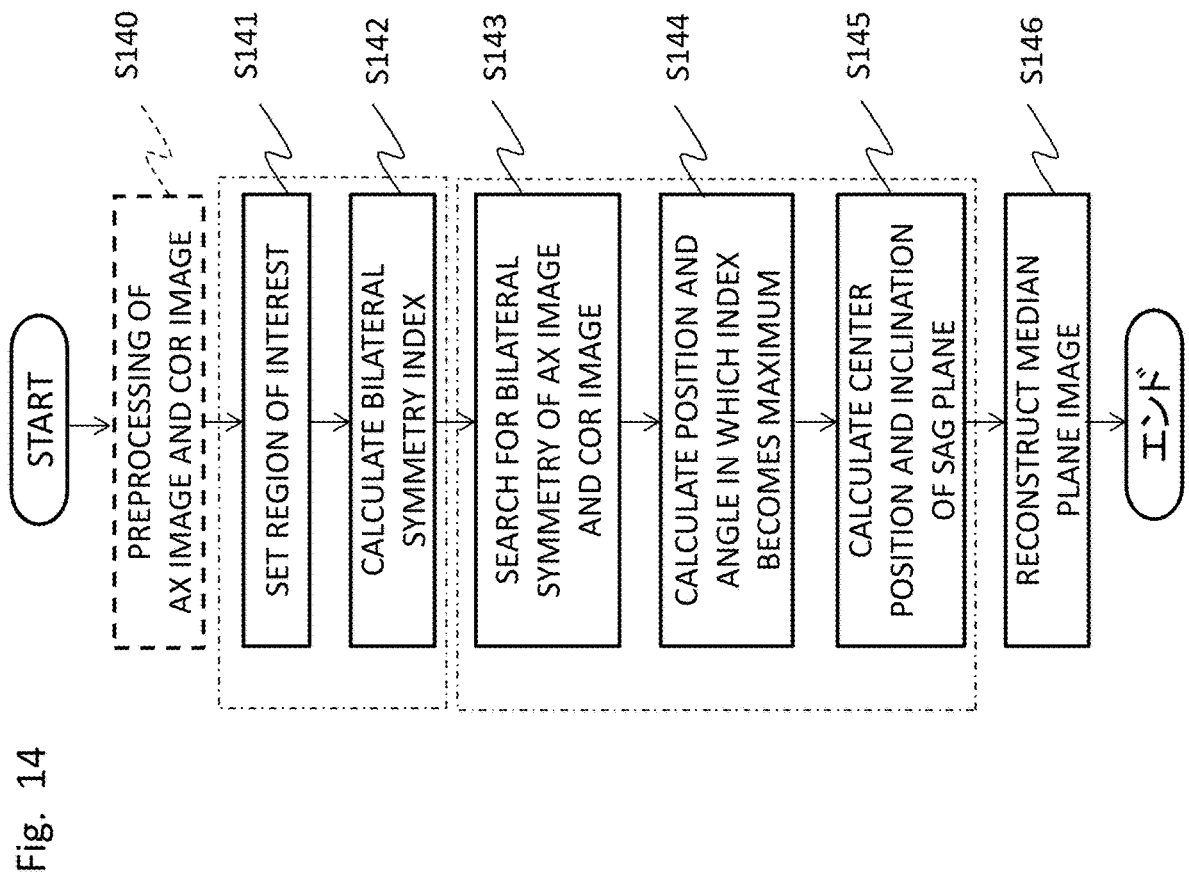
FIG. 14 is a flowchart illustrating a procedure of automatic positioning according to a second embodiment.

First, as illustrated in FIG. 14, the calculation of the median plane image includes step (S141 and S142) of setting the bilateral symmetry index by setting a region of interest and using a pixel value of the region of interest; step (S143 to S145) of extracting an SAG plane imaging position by using the bilateral symmetry index; and step S146 of reconstructing the median plane image.

Hereinafter, each step will be described in detail.

S141 to S142

First, the region of interest having a predetermined size is set with a predetermined point as a reference (S141). The reference point for setting the region of interest and the size of the region of interest are predetermined according to the examination part, and for example, are stored in the storage apparatus 6 (refer to FIG. 1) as a table. Table 1 indicates an example of a table showing a range of the region of interest when processing the respective scout images of the cervical spine, the thoracic spine, and the lumbar spine. In table 1, w (mm) is a width in a left and right direction on the basis of a predetermined point S; h1 (mm) is a length from the point S to an upper end; and h2 (mm) is a length to a lower end. Further, fov is an imaging visual field of the scout image.

TABLE 1

Dimensions of ROI for each spine part

| | AX image | | | COR image | | |
|---|---|---|---|---|---|---|
| Spine part | w [mm] | h1 [mm] | h2 [mm] | w [mm] | h1 [mm] | h2 [mm] |
| Cervical | 100 | 30 | 40 | 100 | 0.425 × fov | 0.25 × fov |
| Thoracic | 200 | 0 | 70 | 200 | 0.425 × fov | 0.425 × fov |
| Lumbar | 100 | 30 | 60 | 100 | 0.425 × fov | 0.25 × fov |

Next, a local image in a predetermined range is extracted from the region of interest set to values shown in Table 1. The bilateral symmetry index is calculated with respect to the extracted local image (S142). Here, when the range of the local image is defined as a horizontal 2N pixel and a vertical M, and the pixel value in coordinates (i, j) of the local image is defined as I[i, j], the bilateral symmetry index $E_{sym}$ can be calculated by Equation (13).

$$E_{sym} = \frac{1}{M} \sum_{j=1}^{M} \frac{\sum_{i=1}^{N}(I[i,j]-I_m[j]) \cdot (I[2N-(i-1),j]-I_m[j])}{\sqrt{\sum_{i=1}^{N}(I[i,j]-I_m[j])^2}\sqrt{\sum_{i=1}^{N}(I[2N-(i-1),j]-I_m[j])^2}} \quad (13)$$

In Equation, $I_m[j]$ is an average value of the pixel value in the j-th row of the local image and is represented by Equation (14).

$$I_m[j] = \frac{1}{2N}\sum_{i=1}^{2N} I[i,j] \quad (14)$$

The bilateral symmetry index $E_{sym}$ calculated in this manner is an average value of ZNCC (Zero-mean Normalized Cross-Correlation) calculated for each row of the local image. $E_{sym}$ indicates that as the value is closer to 1, the symmetry of left and right regions with respect to a center line is higher.

S143 to S145

The imaging position (the position of the median plane) of the SAG plane is extracted using the bilateral symmetry index $E_{sym}$. Therefore, first, a bilateral symmetry line is searched for the scout images of the AX plane and the COR plane (S143). Specifically, an imaging center (x0, y0, z0) of the scout image is defined as a ROI reference point S; $E_{sym}$ is calculated at an interval of one pixel in the left and right direction of ±a predetermined range (for example, ±30 mm); and a position in the left and right direction of ROI where $E_{sym}$ becomes maximum is searched. Next, $E_{sym}$ is calculated by rotating the ROI at an interval of one degree in a predetermined angle range (for example, ±10°), and an angle of a symmetry line where $E_{sym}$ becomes maximum is searched.

Next, a plane passing through the bilateral symmetry line of the scout images of the AX plane and the COR plane is calculated; and by using the calculated plane as an initial value, a position x0' and an angle (an angle θ of a line of intersection on the AX plane and an angle φ0 of a line of intersection on the COR plane) in the left and right direction of a plane where the bilateral symmetry index $E_{sym}$ of the COR plane and the AX plane becomes maximum are calculated by a steepest descent method (S144).

Finally, a column vector r and a row vector c specifying a center position "O" and an inclination of the plane are calculated as a SAG plane imaging position by the following Equation (15) (S145).

$$\begin{cases} o = (x'_0 \quad y_0 \quad z_0) \\ r = (-\sin\theta \quad -\cos\theta \quad 0) \\ c = (-\sin\phi'\cos\theta \quad -\sin\phi'\sin\theta \quad -\cos\phi') \end{cases} \quad (15)$$

In Equation (15), $$\phi' = \arctan(\tan\phi\cos\theta)$$

Step S146

Next, an image of the imaging position calculated from the scout images of a plurality of SAG planes is cut out using the imaging position of the SAG plane calculated in step S145, and the image cut out is used for setting the imaging position of the AX plane. The calculation of the imaging position of the AX plane can be performed by the method (the tissue detection method and the matching process) described in the first embodiment as illustrated in FIG. 6.

According to the embodiment, a position of the median plane is detected using the bilateral symmetry index, and the reconstructed SAG image of the position of the median plane is used, thereby making it possible to improve the accuracy of the imaging position calculation of the AX plane. Further, the position of the median plane specified by the detection of the median plane can also be set as the imaging cross-section position of the SAG plane in the main imaging, and it is possible to accurately execute the main imaging of the SAG plane and the AX plane only with the scout image. Further, instead of reconstructing the image of the position of the median plane, in the positioning imaging, first, imaging of two cross sections of the AX plane and the COR plane is performed, after which the calculation of the imaging position of the SAG plane is performed, and then the scout image of the SAG plane may be acquired at the calculated position.

Modified Example of Second Embodiment

In the embodiment of the calculation method of the SAG plane imaging position of the second embodiment, the position at which the bilateral symmetry index in the region of interest becomes maximum is calculated, however, in order to suppress an influence of bilateral asymmetry on the COR plane, preprocessing may be performed on the scout image on the COR plane (step S140 indicated by a dotted line in FIG. 14). As illustrated in FIGS. 15A and 15B, a Gaussian filter (a) and a second-order differential filter in a head-foot direction (a HF direction) can be used for the preprocessing.

The intervertebral disk structure of the spine can be compared with surrounding tissue by performing such preprocessing, thereby making it possible to put an emphasis thereon. FIGS. 16A and 16B illustrate COR plane scout images before and after the filter process is applied. FIG. 16A illustrates the COR plane scout image before the filter is applied, and FIG. 16B illustrates the image obtained by applying the second-order differential filter after the Gaussian filter is applied. As illustrated with a triangular mark in FIGS. 16A and 16B, a structure of the heart and aorta disappears in the COR image which is second-order differentiated in the HF direction, whereas as indicated by a thick arrow, the intervertebral disk structure of the spine is compared with the surrounding tissue and is more emphasized.

As described above, the bilateral symmetry index is calculated using the image to which the second-order differentiation is applied (FIG. 14: S142). In this case, since information on the tissue structure is lost in most regions, the bilateral symmetry index is calculated by background noise. Then, in the image of the second-order differentiation, the bilateral symmetry index $E_{sym}$ is calculated by Equation (16) using a weight $w_j$ in which a part having a high pixel value $I[i,j]$ becomes higher specific gravity.

$$E_{sym} = \frac{1}{M}\sum_{j=1}^{M} w_j \frac{\sum_{i=1}^{N}(I[i,j]-I_m[j])\cdot(I[2N-(i-1),j]-I_m[j])}{\sqrt{\sum_{i=1}^{N}(I[i,j]-I_m[j])^2}\sqrt{\sum_{i=1}^{N}(I[2N-(i-1),j]-I_m[j])^2}} \quad (16)$$

Here, the weight $w_j$ is calculated by Equation (17) using the maximum value $I_{m \cdot max}$ of $I_m[j]$ and the minimum value $I_{m \cdot min}$ thereof.

$$w_i = \frac{2}{1+\exp\left[-10\frac{I_m[j]-I_{m,min}}{I_{m,max}-I_{m,min}}\right]} - 1 \quad (17)$$

Detecting the median plane and reconstructing the image of the median plane in steps S143 to S146 of FIG. 14 using the bilateral symmetry index $E_{sym}$ calculated by Equation 16 is the same as that of the second embodiment. According to the modified example, it is possible to improve the calculation accuracy of the imaging position of the SAG plane in the subsequent steps S143 to S145 by performing the preprocessing for emphasizing the anatomical feature in the image used for detecting the median plane and using the calculated bilateral symmetry index.

Third Embodiment

The embodiment provides a method for detecting and coping with a case in which searching for the imaging position of the SAG plane fails and a case in which positioning becomes difficult due to the curvature of the spine, and the like. Specifically, with respect to the imaging position of the SAG plane calculated in the first embodiment or the second embodiment, a means for determining the reliability thereof is provided in the embodiment, and as a result of the determination, when it is determined that the reliability does not exist, for example, the axial cross section is set as the imaging position.

Figure 17:
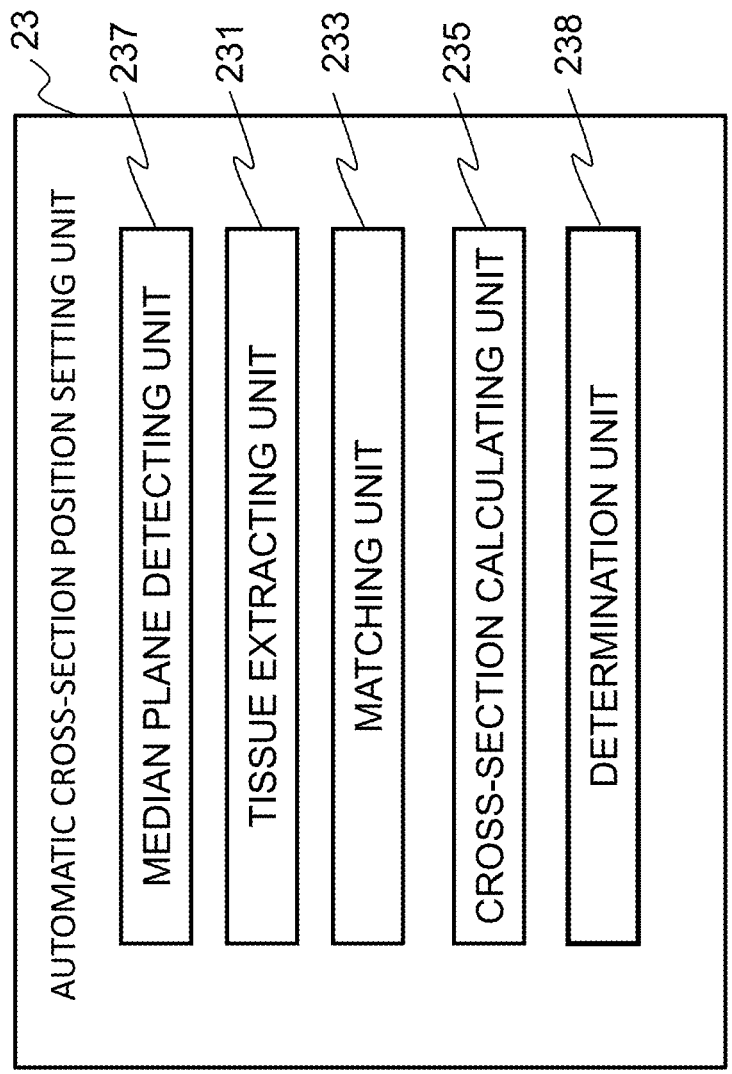
FIG. 17 is a functional block diagram of an automatic cross-section position setting unit according to a third embodiment.

FIG. 17 illustrates a configuration of the automatic cross-section position setting unit 23 according to the embodiment. In FIG. 17, the same elements as those of FIG. 13 indicating the configuration of the automatic cross-section position setting unit 23 according to the second embodiment are denoted by the same reference signs. As illustrated in FIG. 17, in the embodiment, a determination unit 238 is added as a function of the automatic cross-section position setting unit 23. Further, when the embodiment is applied to the first embodiment, the median plane detecting unit can be omitted. Since functions other than the determination unit 238 are the same as those of the automatic cross-section position setting unit 23 in the first embodiment and the second embodiment, hereinafter, the function of the determination unit 238 will be mainly described.

Figure 18:
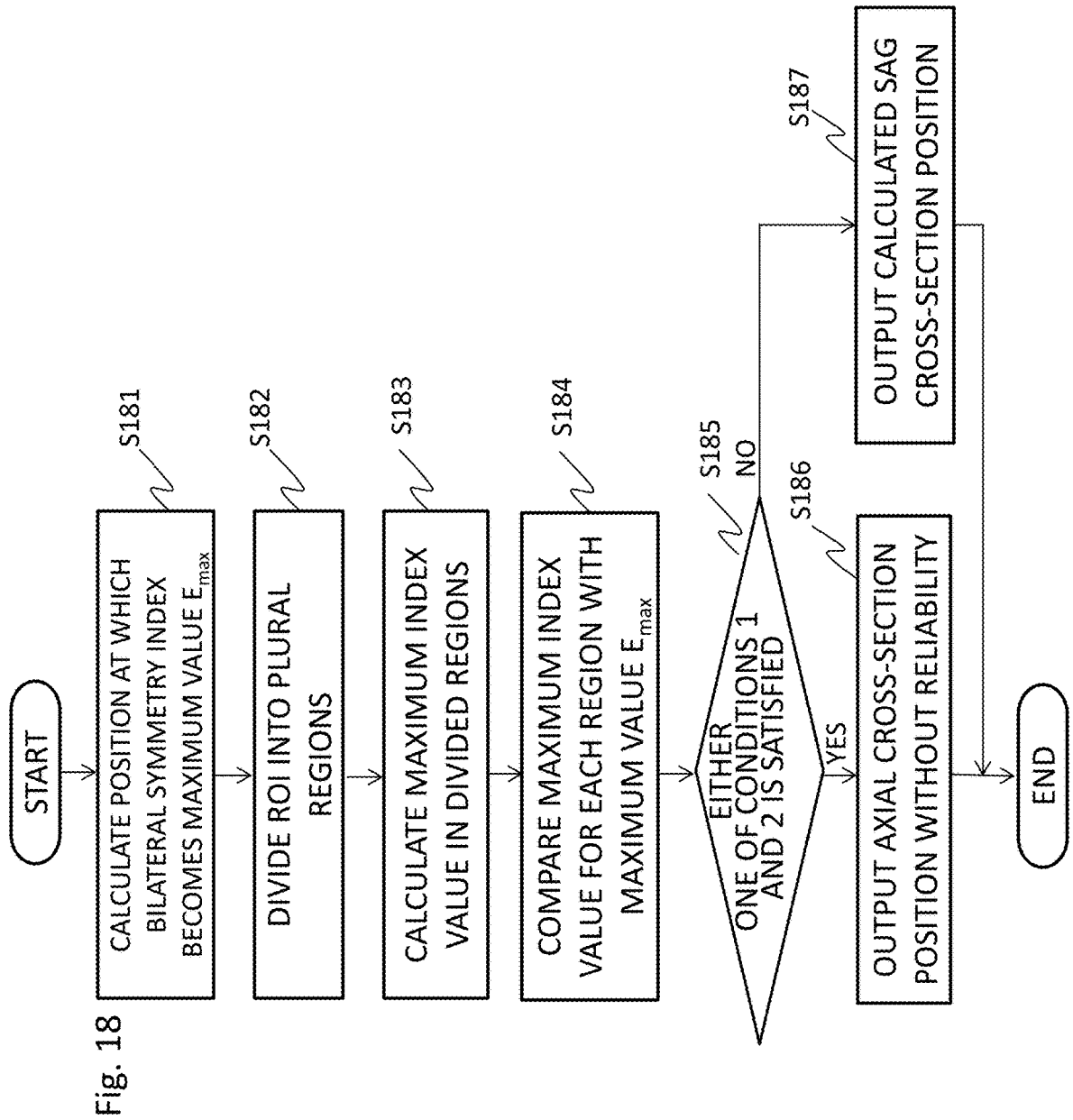
FIG. 18 is a flowchart illustrating a procedure of determining an automatic positioning result according to the third embodiment.

An embodiment of a reliability determination procedure will be described with reference to FIG. 18.

First, when calculating the SAG plane imaging position, the maximum value among the bilateral symmetry indexes calculated from the scout images of the COR plane and the AX plane is defined as $E_{sym \cdot max}$, and the coordinate in the left and right direction of the SAG plane imaging position which becomes the maximum value is defined as $x_{cal}$ (S181).

On the other hand, ROI in which the bilateral symmetry index is calculated in the scout image of the COR plane is divided into five in the HF direction (S182). Next, $E_{sym}$ is calculated at an interval of one pixel in a range of ±30 mm in the left and right direction for each divided region, and the coordinates xdiv·i (i=1, . . . , 5) in the left and right direction where $E_{sym}$ becomes maximum are calculated (S183). The coordinates xdiv·i calculated here are considered to be approximately equal to the position in the left and right direction of the vertebral body in each of the divided regions.

Next, an average value v1 and a standard deviation v2 of the difference between $x_{cal}$ and xdiv·i are obtained. The reliability of the calculated SAG plane imaging position is determined using the maximum value of the bilateral symmetry index, the average value v1, and the standard deviation v2 (S184). Specifically, whether or not $E_{sym·max}$ is equal to or less than a predetermined threshold value (a condition 1), or whether or not v1 and v2 are equal to or greater than the predetermined threshold value (different from the threshold value of $E_{sym·max}$) is determined, after which when either one of the conditions 1 and 2 is satisfied, it is determined that the reliability of the calculation result does not exist (S185), and an axial cross-section position is outputted (S186).

For example, the threshold value is represented as follows:

$E_{sym·max} \leq 0.025$    Condition 1:

$|v1| \geq 10$ and $v2 \geq 15$    Condition 2:

When either of the above-described conditions is not satisfied, it is determined that the reliability of the calculation result exists (S185), and the calculated SAG plane main imaging position is outputted (S187).

According to the embodiment, in the case where searching for the imaging position of the SAG plane fails and the case where positioning becomes difficult due to the curvature of the spine, it is possible to avoid the risk of imaging at an inappropriate position and redoing of the imaging caused thereby by determining the reliability of an automatic positioning result.

Fourth Embodiment

In the first embodiment and the second embodiment, the cross-section position of the main imaging is set using the scout image, however, the embodiment is characterized in that a means for correcting the set imaging cross-section position using the image of the main imaging is provided. For example, the imaging cross-section position of the set second cross section is corrected using the image of the first cross section acquired by the main imaging.

Figure 19:
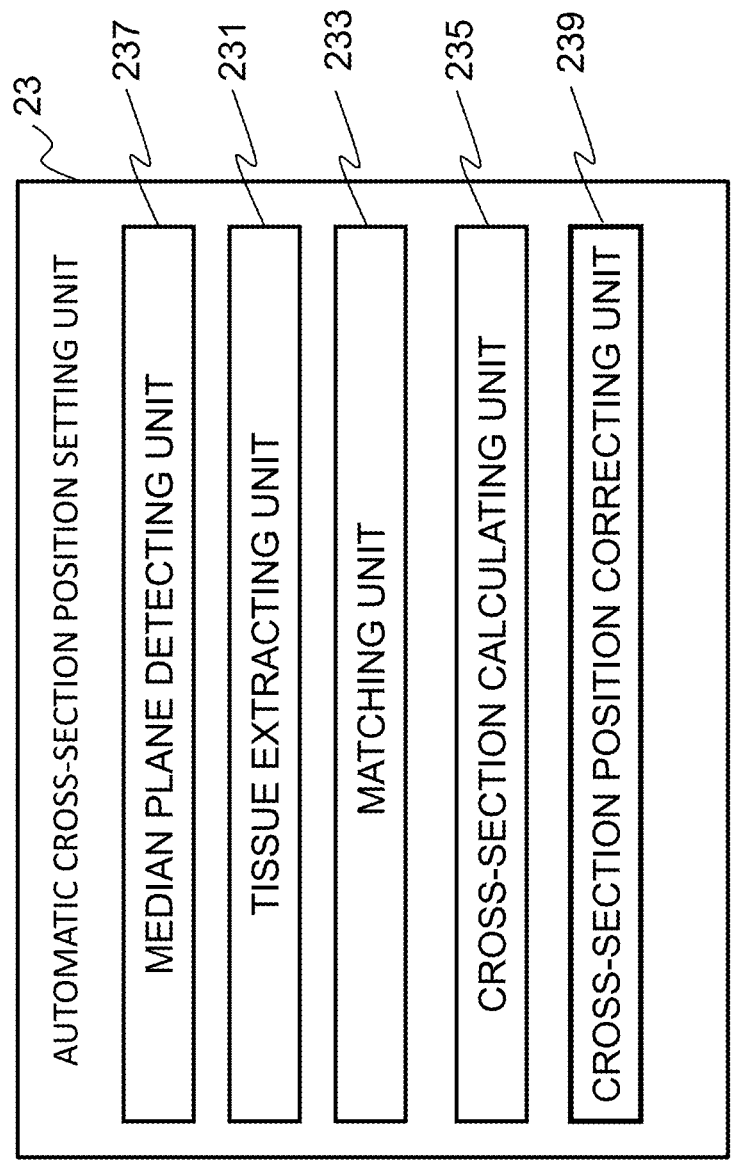
FIG. 19 is a functional block diagram of an automatic cross-section position setting unit according to a fourth embodiment.

FIG. 19 illustrates a configuration of the automatic cross-section position setting unit according to the embodiment. In FIG. 19, the same elements as those of FIG. 13 are denoted by the same reference signs, and a redundant description thereof will be omitted. The automatic cross-section position setting unit 23 according to the embodiment includes a cross-section position correcting unit 239 in addition to the tissue extracting unit 231, the matching processing unit 233, the imaging cross-section calculating unit 235, and the median plane detecting unit 237. Even in the embodiment, the methods for the tissue detection and the matching process are the same as those of the first embodiment. Further, the method for detecting the median plane by the median plane detecting unit 237 is the same as that of the second embodiment. However, when the scout image is used for the automatic positioning without the reconstruction, it is also possible to omit the function of the median plane detecting unit 237.

Figure 20:
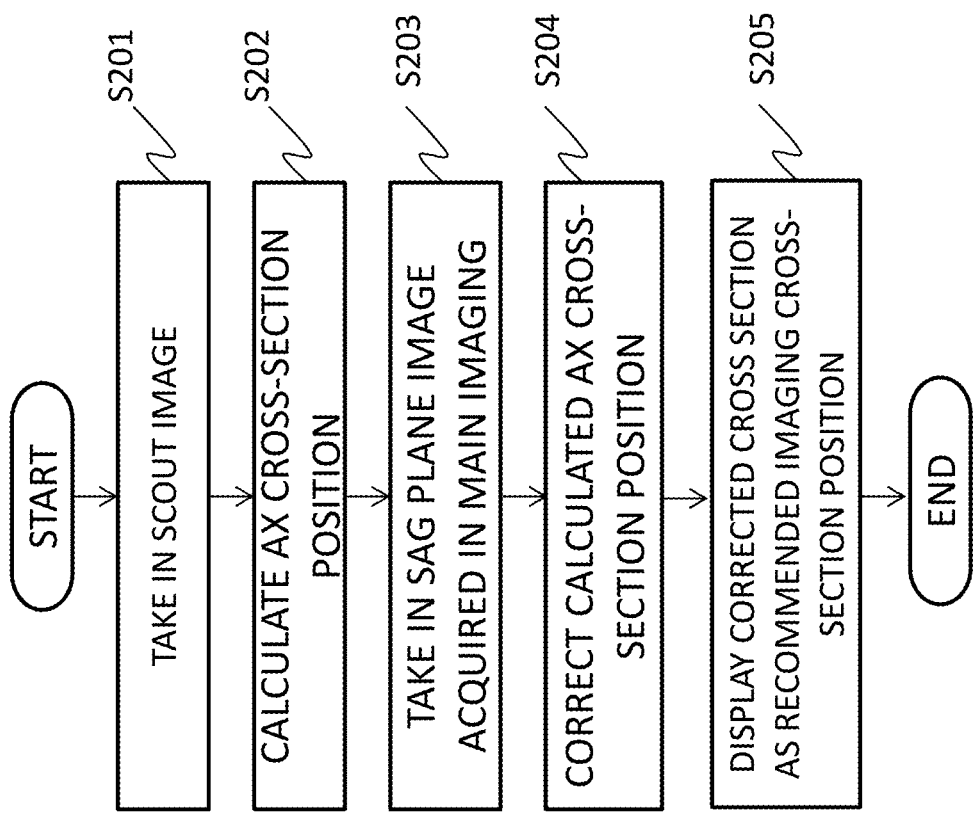
FIG. 20 is a flowchart illustrating a procedure of automatic positioning according to the fourth embodiment.

Hereinafter, the procedure of setting the cross-section position in the embodiment will be described with reference to FIG. 20.

First, the scout image of the three-axis planes acquired by positioning imaging is taken in (S201). The cross-section position of the SAG plane in the positioning imaging may be determined by specifying the median plane image from the AX plane image and the COR plane image by the method described in the third embodiment or the modified example thereof.

Next, the imaging cross-section position (the SAG plane and the AX plane) of the main imaging is determined (S202). The imaging cross-section position of the AX plane can be calculated by performing the method described in the first embodiment, that is, the tissue extraction and the matching process by using the scout image of the SAG plane or the SAG image reconstructed by using the position of the median plane calculated from the AX plane image and the COR plane image. At this time, the main imaging is started, and the imaging is performed at the imaging position of the SAG plane determined in S202, whereby the image of the SAG plane is acquired.

The cross-section position correcting unit 239 receives the main imaged image of the SAG plane acquired in the main imaging from the image creating unit 21 (FIG. 2) (S203), and then corrects the imaging cross-section position of the AX plane determined in S202 (S204). Specifically, the anatomical feature of the specific tissue (the intervertebral disk) is extracted from the main imaged image of the SAG plane, and the calculated position of the specific tissue (the intervertebral disk) is compared with the SAG image used for setting the imaging cross-section position of the AX plane. In the comparison therebetween, intervertebral disk positions calculated in the same extraction range (a range where the matching process is performed) are compared with each other in order, and then a difference of coordinates of the positions is obtained. When the difference exceeds a predetermined threshold value with respect to a certain intervertebral disk, the AX plane specified from the position of the intervertebral disk is corrected by specifying the AX plane again from the position of the main imaged image. Alternatively, when a distance between the intervertebral disks is compared therewith and a difference of the distance between the intervertebral disks exceeds a predetermined threshold value, it is determined that the detection of the intervertebral disk failed in the scout image, and the AX plane specified from the two intervertebral disks which are the distance between the intervertebral disks is specified again from the position of the main imaged image, thereby correcting the AX plane.

The corrected AX plane is displayed on the display unit 4 as a recommended imaging plane (S205). When the recommended imaging plane of the AX plane is already displayed prior to the main imaging, the displayed recommended imaging plane is updated to the corrected recommended imaging plane.

Since the above-described correction can be realized by the feature extraction from the main imaged image and the comparison between images, the calculation time is short. Accordingly, as in the modified example of the first embodiment, the automatic setting of the AX plane can be more promptly performed in comparison with a case in which the automatic positioning is performed by using the main imaged image. As a result, even when a series of the main imaging is continuously performed, it is possible to perform the imaging of the AX plane after the imaging of the SAG plane without large delay. Particularly, as illustrated in FIG. 3, in the examination protocol that performs the imaging of two kinds of the SAG planes and the imaging of two kinds of the AX planes, the imaging at the corrected AX plane position can be performed immediately after the imaging of the second SAG plane by correcting the imaging cross-section position according to the embodiment during the imaging of the second SAG plane.

The embodiments of the present invention have been described hereinabove, and the features common to the respective embodiments are described as follows.

An MRI apparatus includes: an imaging unit that selects a desired imaging plane of a subject and acquires a nuclear magnetic resonance signal generated from the imaging plane; a signal processing unit that processes the nuclear magnetic resonance signal acquired from the imaging unit; a control unit that controls the imaging unit and the signal processing unit; and an imaging cross-section position setting unit that automatically sets a position of the imaging plane, wherein the imaging cross-section position setting unit includes: a tissue extracting unit that extracts a specific tissue by using an image acquired in advance by the imaging unit; a matching unit that performs a matching process on the specific tissue extracted by the tissue extracting unit by using a model (a template) of the specific tissue; and a cross-section calculating unit that calculates a cross-section position including the specific tissue specified through the matching process.

The control unit of the MRI apparatus performs the following control.

That is, imaging of the imaging unit performs a step of imaging a positioning image of a subject including a spine; a first imaging step of imaging a first cross section including the spine and extending along a longitudinal direction of the spine; and a second imaging step of imaging a second cross section in a direction of traversing the spine, and the automatic imaging position setting unit performs an automatic positioning step of automatically setting a position of the cross section to be imaged in the second imaging step, wherein the automatic positioning step includes: a tissue detection step of detecting a specific tissue of the spine by using the positioning image or an image including the spine acquired in the first imaging step; a matching step of performing a matching process between a position of the specific tissue of the spine detected in the tissue detection step and a spine model; and a cross-section calculation step of calculating a position of the second cross section based upon the position of the specific tissue specified by matching with the spine model in the matching step.

As described above, the present invention is characterized in that the issue extraction and the matching using the extracted tissue are combined with each other in the automatic setting of the position of the imaging plane in the MRI. The means for realizing the above-described feature is not limited to the computer, and the software and hardware of the signal processing unit illustrated in the embodiment, and a part of the processes can be also realized by a computer independent from the MRI apparatus, software on the cloud, and the like. Further, in the present invention, a part of the elements may be excluded among the elements illustrated in the embodiments, or, alternatively, a well-known element not illustrated in the embodiments may be added thereto.

What is claimed is:

1. A magnetic resonance imaging apparatus, comprising:
  an imager configured to select a desired imaging plane of a subject to acquire a nuclear magnetic resonance signal generated from the imaging plane;
  a signal processor configured to process the nuclear magnetic resonance signal acquired from the imager;
  a controller configured to control the imager and the signal processor; and
  the signal processor configured to automatically set a position of the imaging plane, wherein
  the signal processor is configured to:
  extract a plurality of intervertebral disks to detect a position and size of each of the plurality of intervertebral disks, using an image acquired in advance by the imager,
  perform a matching process with a spine model based upon information of the position and size of each intervertebral disk, detected by the signal processor, and calculate a cross-section position including the intervertebral disks specified through the matching process;
  calculate a maximum value $E_{sym,max}$ from among bilateral symmetry indexes $E_{sym}$ from each of a coronal plane imaging position and an axial plane imaging position;
  calculate a parameter $x_{cal}$ as coordinates in a left and a right direction of a sagittal plane imaging position which become a maximum value;
  calculate coordinates xdiv.i in left and right directions where $E_{sym}$ becomes maximum for the coronal plane, where i is an integer, and wherein in images obtained by dividing a coronal image into i regions, xdiv.i is defined as a left and a right direction where $E_{sym}$ for the coronal plane becomes maximum in the i-th region;
  calculate an average value v1 and a standard deviation v2 of the difference between $x_{cal}$ and xdiv.i.

2. The magnetic resonance imaging apparatus according to claim 1, wherein the signal processor is configured to perform the matching process while deforming the template of the spine model under a certain constraint.

3. The magnetic resonance imaging apparatus according to claim 1, wherein the imager is configured to perform positioning imaging for determining the position of the imaging plane and main imaging for a plurality of cross sections including a first cross section and a second cross section crossing each other, and the signal processor is configured to set an imaging cross-section position of the second cross section using an image of the first cross section acquired by the positioning imaging or the main imaging.

4. The magnetic resonance imaging apparatus according to claim 3, wherein the first cross section is a sagittal plane, and the second cross section is an axial plane.

5. The magnetic resonance imaging apparatus according to claim 3, wherein the signal processor further is configured to extract an anatomical feature of an image acquired by the positioning imaging to detect a median plane, and reconstruct and use an image of a position detected by the signal processor as the image of the first cross section.

6. The magnetic resonance imaging apparatus according to claim 1, wherein the signal processor is further configured to determine reliability of the cross-section position calculated by the signal processor, and, when the signal processor determines that the reliability is low, set a position of a cross section (axial cross section) passing through an apparatus coordinate axis used for setting the cross-section position as an imaging cross-section position.

7. The magnetic resonance imaging apparatus according to claim 1, further comprising: a display controller configured to cause a display to display the cross-section position set by the signal processor as a recommended imaging cross-section position.

8. The magnetic resonance imaging apparatus according to claim 1, wherein the signal processor is further configured to correct the cross-section position calculated by the signal processor by using an image acquired in main imaging.

9. The magnetic resonance imaging apparatus according to claim 1, wherein the signal processor is configured to perform the extraction of the intervertebral disks using a machine learning algorithm learned by learning data of the intervertebral disks.

10. The magnetic resonance imaging apparatus according to claim 1, wherein the signal processor is configured to perform the extraction using an adaptive boosting method.

11. The magnetic resonance imaging apparatus according to claim 1, wherein the signal processor is configured to perform the matching process using an active shape model method.

12. The magnetic resonance imaging apparatus according to claim 1, wherein the signal processor is configured to arrange the plurality of intervertebral disks in order from a tissue as a reference to perform the matching process with the spine model according to the order.

13. The magnetic resonance imaging apparatus according to claim 1, wherein when either one of Condition 1 or Condition 2 is met, the signal processor is configured to output an axial cross-section position, wherein Condition 1 is $E_{sym,max} \leq 0.025$, and Condition 2 is $|v1| \geq 10$ and $v2 \geq 15$.

14. A method for controlling a magnetic resonance imaging apparatus including an imager and a signal processor configured to automatically position an imaging position, comprising:
   imaging, using imaging of the imager, a positioning image of a subject including a spine,
   a first imaging, using the imaging of the imager, a first cross section including the spine and extending along a longitudinal direction of the spine, and
   a second imaging, using the imaging of the imager, a second cross section in a direction of traversing the spine; and
   automatically setting, using the signal processor, a position of the cross section to be imaged in the second imaging, wherein
   the automatically setting includes:
   detecting a plurality of intervertebral disks using the positioning image or an image including the spine acquired in the first imaging,
   performing a matching process between a position of the plurality of intervertebral disks detected in the plurality of intervertebral disks tissue detection and a spine model, and
   calculating a position of the second cross section based upon the positions of the plurality of intervertebral disks specified by matching with the spine model in the matching;
   calculating a maximum value $E_{sym,max}$ from among bilateral symmetry indexes $E_{sym}$ from each of a coronal plane imaging position and an axial plane imaging position;
   calculating a parameter $x_{cal}$ as coordinates in a left and a right direction of a sagittal plane imaging position which become a maximum value;
   calculating coordinates xdiv.i in left and right directions where $E_{sym}$ becomes maximum for the coronal plane, where i is an integer, and wherein in images obtained by dividing a coronal image into i regions, xdiv.i is defined as a left and a right direction where $E_{sym}$ for the coronal plane becomes maximum in the i-th region;
   calculating an average value vi and a standard deviation v2 of the difference between $x_{cal}$ and xdiv.i.

15. The control method according to claim 14, wherein the automatic positioning further includes creating a median plane image using the positioning image, and the position of the second cross section is set using the median plane image.

16. A non-transitory computer readable medium storing a program for auto-setting of an imaging plane, the program, when executed by the computer, causing the computer to execute operations comprising:
   receiving positioning images of a sagittal plane, an axial plane, and a coronal plane imaged by a magnetic resonance imaging apparatus;
   determining an image of the sagittal plane for determining an imaging cross-section position of the axial plane using at least one of the positioning images of the axial plane and the coronal plane; and
   determining the imaging cross-section position of the axial plane using the determined image of the sagittal plane, wherein
   the determining the imaging cross-section position of the axial plane includes:
   extracting a plurality of intervertebral disks from the determined image of the sagittal plane to detect a position and size of each of the plurality of intervertebral disks;
   performing a matching process with the spine model, based upon information of the detected position and size of each of the plurality of intervertebral disks; and
   calculating the imaging cross-section position of the axial plane using a matching process result;
   calculating a maximum value $E_{sym,max}$ from among bilateral symmetry indexes $E_{sym}$ from each of a coronal plane imaging position and an axial plane imaging position;
   calculating a parameter $x_{cal}$ as coordinates in a left and a right direction of a sagittal plane imaging position which become a maximum value;
   calculating coordinates xdiv.i in left and right directions where $E_{sym}$ becomes maximum for the coronal plane, where i is an integer, and wherein in images obtained by dividing a coronal image into i regions, xdiv.i is defined as a left and a right direction where $E_{sym}$ for the coronal plane becomes maximum in the i-th region;
   calculating an average value vi and a standard deviation v2 of the difference between $x_{cal}$ and xdiv.i.

* * * * *